(12) United States Patent
Kim et al.

(10) Patent No.: US 10,574,257 B2
(45) Date of Patent: Feb. 25, 2020

(54) PREDICTIVE DIGITAL AUTORANGING ANALOG-TO-DIGITAL CONVERTER

(71) Applicant: The Regents of the University of California, Oakland, CA (US)

(72) Inventors: Chul Kim, La Jolla, CA (US);
Siddharth Joshi, San Diego, CA (US);
Gert Cauwenberghs, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/271,739

(22) Filed: Feb. 8, 2019

(65) Prior Publication Data

US 2019/0253069 A1 Aug. 15, 2019

Related U.S. Application Data

(60) Provisional application No. 62/628,671, filed on Feb. 9, 2018.

(51) Int. Cl.
| | |
|---|---|
| *H03M 3/00* | (2006.01) |
| *H03M 7/16* | (2006.01) |
| *H03F 3/45* | (2006.01) |
| *A61B 5/04* | (2006.01) |

(52) U.S. Cl.
CPC ......... *H03M 3/422* (2013.01); *A61B 5/04001* (2013.01); *H03F 3/45215* (2013.01); *H03M 3/464* (2013.01); *H03M 3/496* (2013.01); *H03M 7/165* (2013.01)

(58) Field of Classification Search
CPC ...... H03M 3/422; H03M 3/496; H03M 3/464; H03F 3/45215; A61B 5/04001

USPC .................................................. 341/140–155
See application file for complete search history.

(56) References Cited

U.S. PATENT DOCUMENTS

| | | | | | |
|---|---|---|---|---|---|
| 6,127,955 | A | * | 10/2000 | Handel | H03M 1/1038 341/118 |
| 7,567,192 | B2 | * | 7/2009 | Colmer | H03M 3/484 341/118 |
| 2008/0191713 | A1 | * | 8/2008 | Hauer | G01R 27/2605 324/658 |
| 2009/0021408 | A1 | * | 1/2009 | Lee | H03M 3/49 341/143 |
| 2018/0269896 | A1 | * | 9/2018 | Ouzounov | H03M 3/32 |

* cited by examiner

*Primary Examiner* — Lam T Mai

(74) *Attorney, Agent, or Firm* — Mintz Levin Cohn Ferris Glovsky and Popeo, P.C.

(57) ABSTRACT

An apparatus may include a delta sigma modulator. A first portion of the delta sigma modulator may form a digital predictor while a second portion of the delta sigma modulator may form an analog approximator. An output of the analog approximator may be coupled with a quantizer. The digital predictor, the analog approximator, and the quantizer may form a digitizing loop configured to convert an analog input into a digital output. The digital predictor may be configured to generate, based on a polarity of one or more digital outputs from the quantizer, a digital prediction of an expected amplitude of the analog input. The quantizer may be configured to respond to the digital prediction by adjusting a dynamic range of the digitizing loop including by changing a quantization step size used by the quantizer to quantize the analog input. Related methods are also provided.

20 Claims, 18 Drawing Sheets

PREDICTIVE DIGITAL AUTORANGING ANALOG-TO-DIGITAL CONVERTER

CROSS REFERENCE TO RELATED APPLICATIONS

This application claims priority to U.S. Provisional Patent Application No. 62/628,671 filed on Feb. 9, 2018 and entitled "LOW NOISE, LOW POWER ANALOG TO DIGITAL CONVERTER," the contents of which is hereby incorporated by reference in its entirety.

TECHNICAL FIELD

The subject matter disclosed herein relates to signal processing and more specifically to analog to digital conversion.

BACKGROUND

An analog signal may be continuous in both value and time. For example, the analog signal may be associated with a value (e.g., amplitude) for every instant in time. Moreover, the analog signal may take on any value from an infinite set of possible values (e.g., all real numbers $\mathbb{R}$ or all real numbers $\mathbb{R}$ within a limited range). By contrast, a digital signal may be a discrete-time sequence of values from a finite set of discrete values.

SUMMARY

Systems, methods, and articles of manufacture, including apparatuses, are provided for analog-to-digital conversion. In one aspect, there is provided an apparatus for analog-to-digital conversion. The apparatus may include: a first delta sigma modulator, a first portion of the first delta sigma modulator forming a digital predictor, a second portion of the first delta sigma modulator forming an analog approximator, an analog approximation output by the analog approximator being coupled with a quantizer, the digital predictor, the analog approximator, and the quantizer forming a digitizing loop configured to convert an analog input into a digital output, the digital predictor being configured to generate, based at least on a polarity of one or more digital outputs from the quantizer, a digital prediction of an expected amplitude of the analog input, the quantizer being configured to respond to the digital prediction by at least adjusting a dynamic range of the digitizing loop, and the dynamic range of the digitizing loop being adjusted by at least changing a quantization step size used by the quantizer to quantize the analog input.

In some variations, one or more of the features disclosed herein including the following features can optionally be included in any feasible combination. The quantizer may be configured to quantize the analog approximation by at least outputting, for each sample of the analog approximation, a discrete value from a finite set of discrete values corresponding to an amplitude of each sample of the analog approximation. The changing of the quantization step size may modify a range of differences between each discrete value in the finite set of discrete values.

In some variations, the analog input may be oversampled at a frequency above a Nyquist rate.

In some variations, the first delta sigma modulator may include an N quantity of integrators chained to form an n quantity of feedback loops. The digital predictor may include an N–M quantity of integrators. The analog approximator may include a M quantity of integrators. The N–M quantity of integrators may be configured to accumulate the one or more digital outputs from the quantizer. The digital predictor may generate the digital prediction by at least summing a current digital output from the quantizer with an accumulation of one or more previous digital outputs from the quantizer.

In some variations, a digital-to-analog converter may be configured to convert the digital prediction into a corresponding analog signal. A difference between the analog input and the analog signal may be coupled with the analog approximator. The one or more digital outputs from the quantizer may be coupled with the digital predictor in a feedback loop.

In some variations, an amplitude of the analog input may be expected to exceed the dynamic range of the digitizing loop based at least on a threshold quantity of successive digital outputs from the quantizer having a same polarity. The quantizer may respond to the digital prediction by at least increasing the quantization step size to increase the dynamic range of the digitizing loop.

In some variations, an amplitude of the analog input may be expected to settle within the dynamic range of the digitizing loop based at least on a threshold quantity of successive digital outputs from the quantizer having alternating polarities. The quantizer may respond to the digital prediction by at least decreasing the quantization step size to decrease the dynamic range of the digitizing loop.

In some variations, changing a quantization step size used to quantize the analog input may further change a resolution of the quantizer.

In some variations, the dynamic range of the digitizing loop may correspond to a maximum amplitude and/or a minimum amplitude of the analog input the digitizing loop is able to convert.

In some variations, the dynamic range of the digitizing loop may be adjusted by a factor of 2.

In some variations, the apparatus may be a multi-channel neural-signal-acquisition system. The apparatus may further include a second delta sigma modulator. Each of the first delta sigma modulator and the second delta sigma modulator may form one of a plurality of recording channels in the multi-channel neural-signal-acquisition system.

In some variations, the analog input may be a neural electrophysiological signal.

In another aspect, there is provided a method for analog-to-digital conversion. The method may include: receiving, at a delta sigma modulator, an analog input, a first portion of the delta sigma modulator forming a digital predictor, a second portion of the delta sigma modulator forming an analog approximator, an analog approximation output by the analog approximator being coupled with a quantizer, the digital predictor, the analog approximator, and the quantizer forming a digitizing loop configured to convert the analog input into a digital output; generating, by the digital predictor, a digital prediction of an expected amplitude of the analog input, the digital prediction being generated based at least on a polarity of one or more digital outputs from the quantizer; and in response to the digital prediction, adjusting, by the quantizer, a dynamic range of the digitizing loop, the dynamic range of the digitizing loop being adjusted by at least changing a quantization step size used by the quantizer to quantize the analog input.

In some variations, one or more of the features disclosed herein including the following features can optionally be included in any feasible combination. An amplitude of the analog input may be expected to exceed the dynamic range of the digitizing loop based at least on a threshold quantity of successive digital outputs from the quantizer having a same polarity. The quantizer may respond to the digital prediction by at least increasing the quantization step size to increase the dynamic range of the digitizing loop.

In some variations, an amplitude of the analog input may be expected to settle within the dynamic range of the digitizing loop based at least on a threshold quantity of successive digital outputs from the quantizer having alternating polarities. The quantizer may respond to the digital prediction by at least decreasing the quantization step size to decrease the dynamic range of the digitizing loop.

In some variations, the analog input may be converted to the digital output at least by the quantizer quantizing the analog approximation. The analog approximation may be quantized by at least assigning, to each sample of the analog approximation, a discrete value from a finite set of discrete values corresponding to an amplitude of the analog approximation.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a rechargeable battery, it should be readily understood that such features are not intended to be limiting. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, and/or elements.

DETAILED DESCRIPTION

Figure 1A:
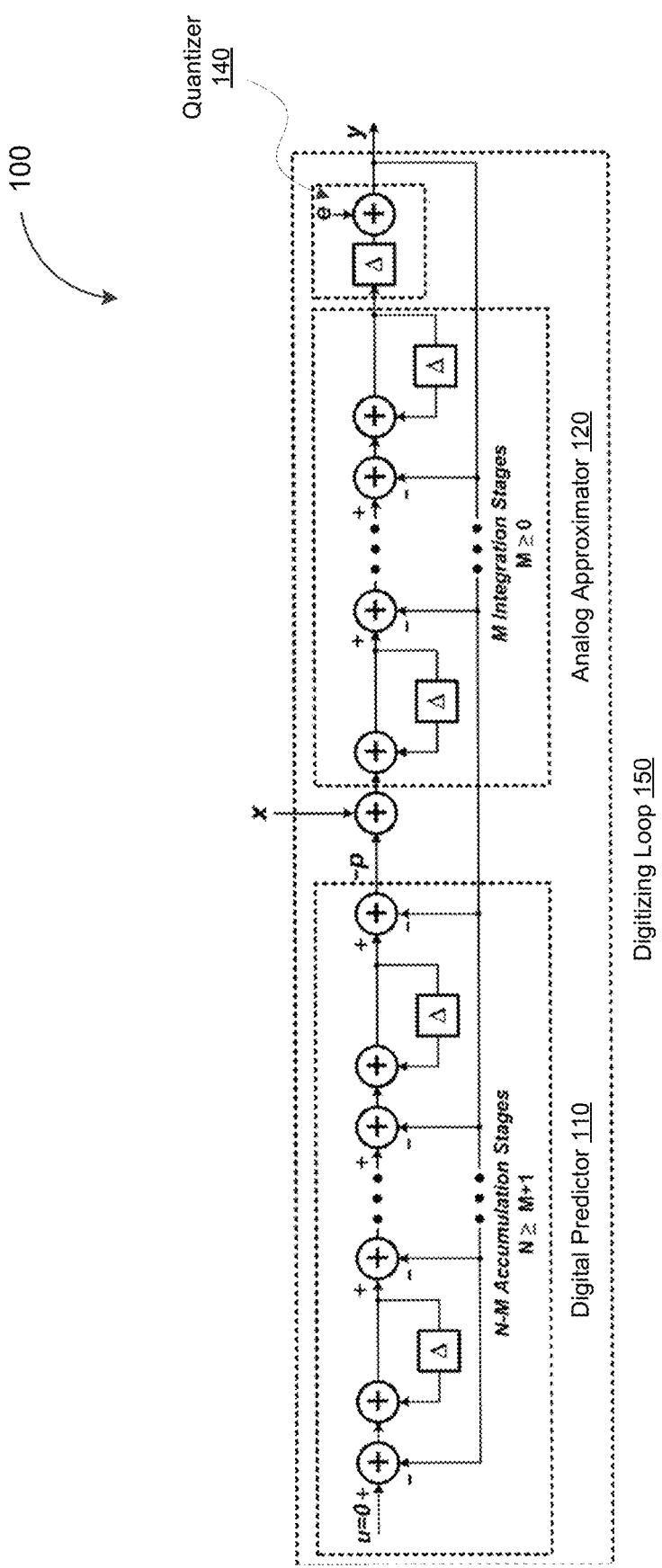
FIG. 1A depicts a block diagram illustrating an example of an analog-to-digital converter, in accordance with some example embodiments.

In order to convert an analog signal to a digital signal, an analog-to-digital converter may sample the analog signal at a certain sampling rate $f_s$ and determine the value (e.g., amplitude) of the analog signal at each sampling interval $$T = \frac{1}{f_s}$$

(e.g., every x microseconds). Moreover, the analog-to-digital converter may encode each sample of the analog signal by mapping the value (e.g., amplitude) of each sample from an infinite set of discrete values (e.g., all real numbers $\mathbb{R}$ or all real numbers $\mathbb{R}$ within a limited range) to a finite set of discrete values. However, a conventional analog-to-digital converter may be unable to resolve noisy input signals with small amplitudes. For example, a neural electrophysiological signal may be a small-amplitude signal (e.g., ranging in tens of microvolts) that is frequently obscured by large-amplitude transients caused by a variety of artifacts including, for example, stimulus artifacts, motion artifacts, and/or the like. The neural electrophysiological signal may be amplified prior to being digitized by a conventional analog-to-digital converter. Nevertheless, the large-amplitude transients accompanying the neural electrophysiological signal may saturate the amplifier such that the amplified neural electrophysiological signal includes distortions that skew the subsequent digitization performed by the analog-to-digital converter. As such, the digital signal output by the analog-to-digital converter may include excessive discrepancies relative to the original neural electrophysiological signal.

In some example embodiments, a predictive digital autoranging (PDA) analog-to-digital converter (ADC) may be configured to resolve noisy small-amplitude input signals. For example, the predictive autoranging analog-to-digital converter may be configured to resolve small-amplitude neural electrophysiological signals including, for example, local field potential (LFP) signals, electrocorticogram (ECoG) signals, and/or the like. The predictive digital autoranging analog-to-digital converter may include an N-th order delta sigma modulator having an n quantity of integrators and an N quantity of feedback loops. A first portion of the N-th order delta sigma modulator including an N–M quantity of purely digital integrators (e.g., accumulators) may form a digital predictor configured to detect large-amplitude transients in the input signal of the predictive digital autoranging analog-to-digital converter. Meanwhile, a second portion of the N-th order sigma delta modulator including an M quantity of integrators may form an analog approximator, whose output feeds into a quantizer having a dynamic range that may be adjusted dynamically to accommodate the large-amplitude transients detected by the digital predictor. The digital predictor, the analog approximator, and the quantizer may form an analog approximator having a variable dynamic range.

In order to provide sufficient loop gain in the digital predictor and to lessen the burden of servicing sufficient loop gain in the remaining M analog integrators in the subsequent analog approximator, the quantity N–M of integrators or accumulation stages in the digital predictor should be at least one. This may enable a reduction in the quantity of analog integrators N–M for the same conversion accuracy, thereby simplifying the hardware complexity of the analog-to-digital converter as well as lowering its power consumption. The quantity N–M of analog integrators may be optimized for signal-to-noise requirements, with lower input-referred noise necessitating larger quantities of analog integration stages. For example, sensitive bio potential recording applications may require at least one analog integration stage (e.g., N–M>0) whereas other applications permitting a larger range of signals at high signal-to-noise ratio may require no integration at all (e.g., N–M=0).

In some example embodiments, the digitizing loop may include an autoranging quantizer whose resolution may be varied in order to adjust the dynamic range of the digitizing loop to accommodate large-amplitude transients detected by the digital predictor. For example, the autoranging quantizer may assign, to each sample of the input signal, one value from a finite set of discrete values. The dynamic range of the digitizing loop may correspond to the maximum and/or minimum amplitude of the input signal that may be encoded by the autoranging quantizer. However, it should be appreciated that the dynamic range of the digitizing loop may depend on the resolution of the autoranging quantizer but not the actual magnitude of the input signal. The resolution of the autoranging quantizer may be varied by changing a quantization step size such that the same finite set of discrete values may be used to encode different magnitudes of the input signal. Accordingly, the autoranging quantizer may respond to the digital predictor detecting a large-amplitude transient in the input signal that exceeds the dynamic range of the digitizing loop by increasing the quantization step size (e.g., by a factor of 2) to expand the dynamic range of the digitizing loop. Alternatively, the autoranging quantizer may respond to the digital predictor detecting that the amplitude of the input signal is settling within the dynamic range of the digitizing loop by decreasing the quantization step size (e.g., by a factor of 2) to contract the dynamic range of the digitizing loop.

In some example embodiments, the quantization step size of the digitizing loop may be reduced until the quantization step reaches the least significant bit (LSB) level of a digital-to-analog converter (DAC) generating the reference for the analog signal based on the digital prediction. The least significant bit level of a digital-to-analog converter may refer to the smallest increment that may be output by the digital-to-analog converter whereas the most significant bit level of the digital-to-analog-converter may refer to the largest increment that may be output by the digital-to-analog converter. As such, digital autoranging may permit full-scale operation with resolution-limited performance for small-amplitude signals at the digital-to-analog converter least significant bit level, and with fast recovery to large transients at the digital-to-analog converter most significant bit (MSB) level.

In some example embodiments, the input signal to the predictive digital autoranging analog-to-digital converter may be coupled directly with the analog approximator instead of the digital predictor. For instance, the input signal coupled with the digital predictor may be zeroed. Avoiding coupling the input signal with the digital predictor may increase the stability of the N-th order delta sigma modulator forming the predictive digital autoranging analog-to-digital converter. For example, the predictive digital autoranging analog-to-digital converter may remain saturation free even when the analog approximator applies only single-bit quantization to a noisy small-amplitude signal that may be frequently contaminated with large-amplitude transients. By contrast, coupling the input signal to the digital predictor may render the predictive digital autoranging analog-to-digital converter more prone to saturation as well as increase the complexity of the circuitry implementing the predictive digital autoranging analog-to-digital converter.

Figure 1B:
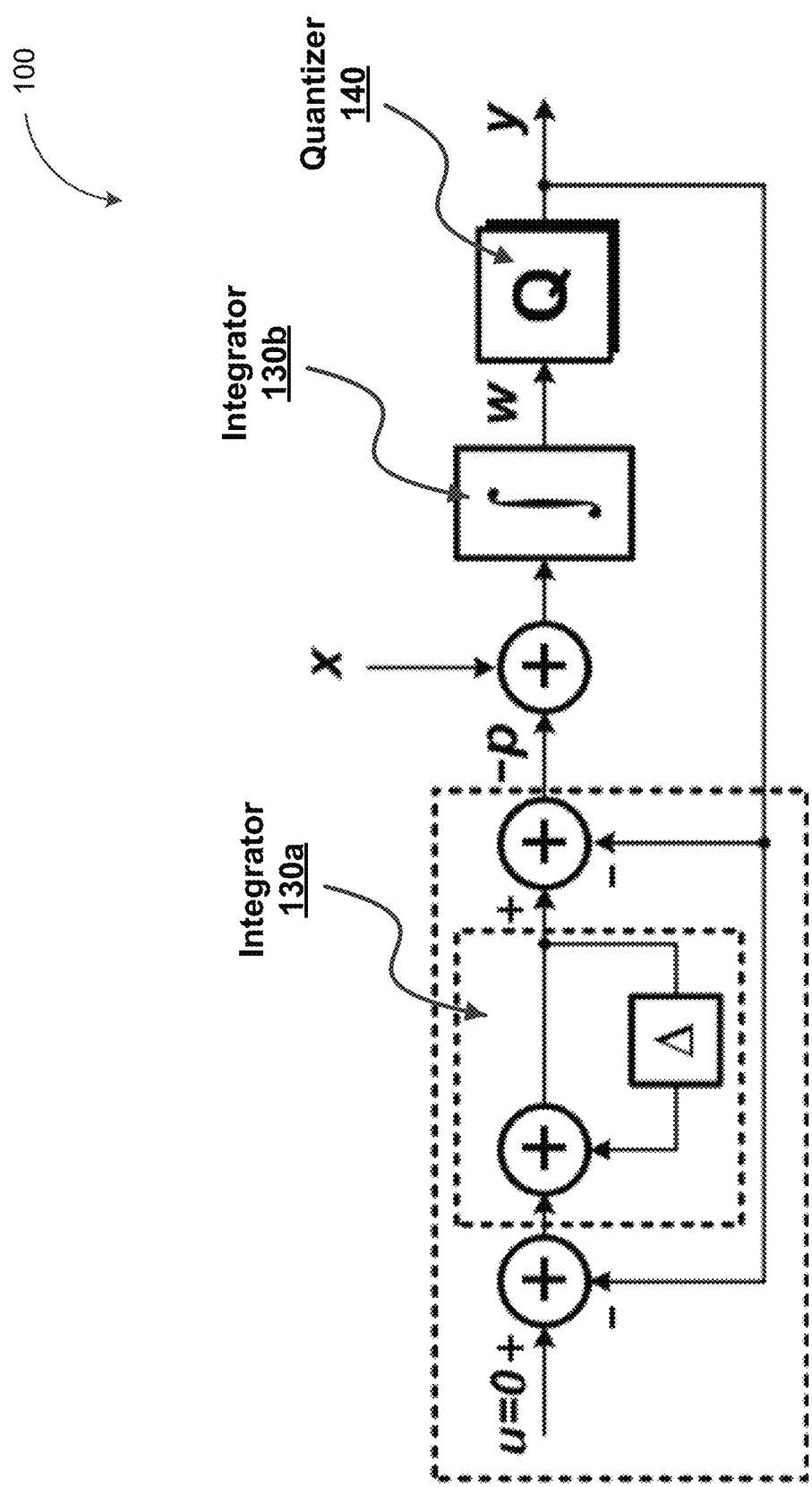
FIG. 1B depicts a system diagram illustrating an example of an analog-to-digital converter, in accordance with some example embodiments.
Figure 1C:
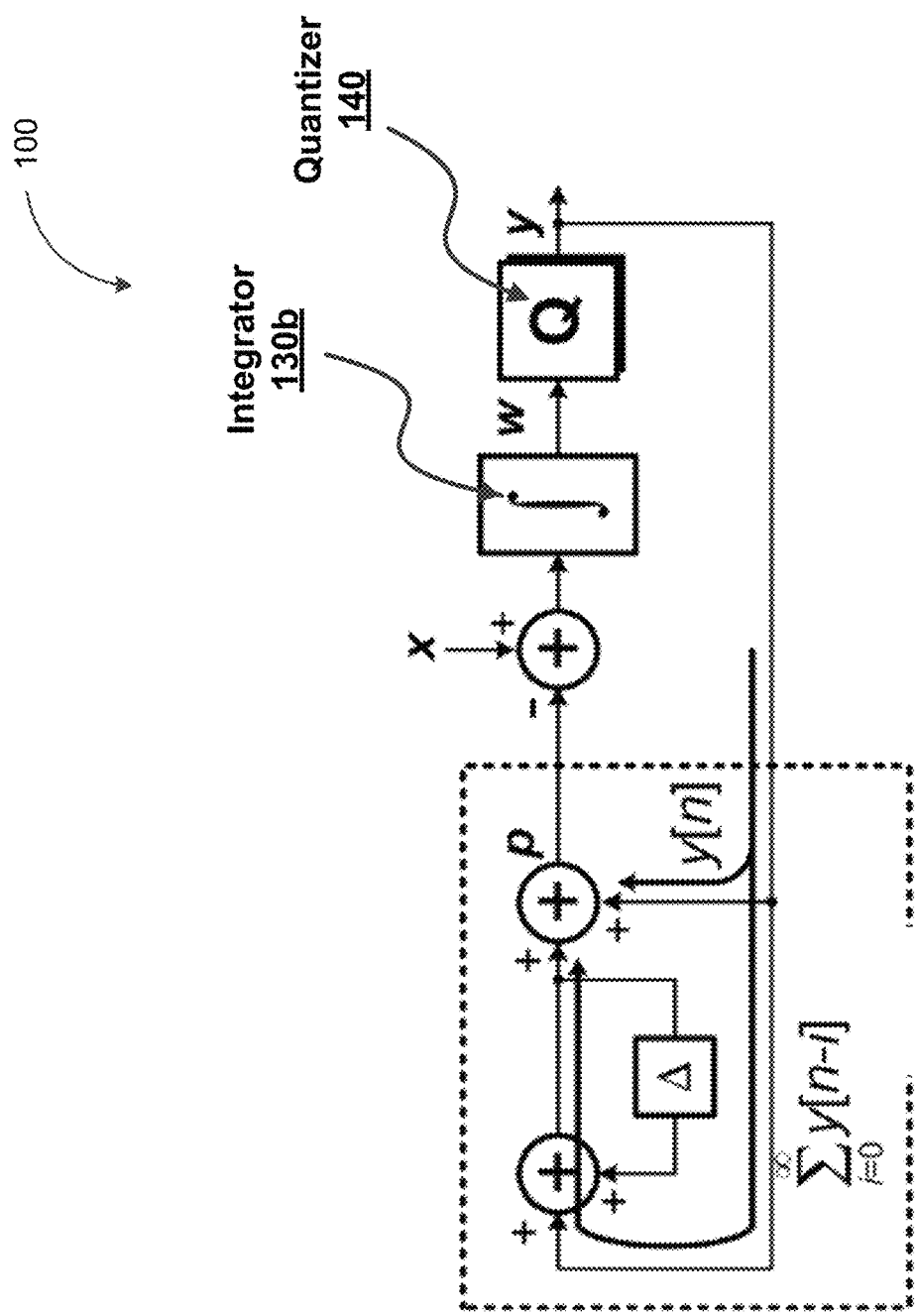
FIG. 1C depicts a system diagram illustrating an example of an analog-to-digital converter, in accordance with some example embodiments.

FIGS. 1A-C depict block diagrams illustrating an example of an analog-to-digital converter 100, in accordance with some example embodiments. Referring to FIGS. 1A-C, the analog-to-digital converter 100 may be a predictive digital autoranging analog-to-digital converter that includes a digital predictor 110, an analog approximator 120, and a quantizer 140. As shown in FIG. 1A, the digital predictor 110, the analog approximator 120, and the quantizer 140 may form a digitizing loop 150. In some example embodiments, the analog-to-digital converter 100 may be coupled to each one of a plurality of recording channels forming a multi-channel (e.g., 16-channel) neural recording system implemented on a millimeter-size chip.

In some example embodiments, the analog approximator 120 may generate, based on an analog input x coupled directly with the analog approximator 120, a corresponding digital output y by at least sampling and encoding the analog input x. The quantizer 140 may generate the digital output y by at least assigning, to each sample of the analog input x, one value from a finite set of discrete values. Meanwhile, the digital predictor 110 may generate, based on the digital output y, a digital prediction p of the expected amplitude of the analog input x. The expected amplitude of the analog input x may exceed the dynamic range of the analog approximator 120 if the analog input x includes one or more large-amplitude transients. For instance, the analog input x may be a small-amplitude neural electrophysiological signal that is frequently contaminated with large-amplitude transients caused by a variety of artifacts including, for example, stimulus artifacts, motion artifacts, and/or the like.

As noted, in some example embodiments, the digital predictor 110 may generate the digital prediction p to be representative of the expected amplitude of the analog input x, given the history of previous digital outputs y. The digital prediction p from the digital predictor 110 may trigger a change in the resolution of the digital feedback from the quantizer 140 as the quantization step size of the quantizer 140 is adjusted to vary the dynamic range of the digitizing loop 150. For example, the resolution of the quantization may be increased from a single bit to multiple bits through the multiple stages of digital accumulation. Example waveforms for the digital prediction p for a step in the analog input x are illustrated in FIG. 2B.

Referring to FIGS. 1A-B, in some example embodiments, the analog-to-digital converter 100 may be an N-th order delta sigma modulator configured to oversample the analog input x, for example, by sampling the analog input x at a frequency above the Nyquist rate (e.g., twice the bandwidth of the analog input x). The N-th order delta sigma modulator may include an n quantity of integrators that are chained via summation blocks. For instance, the digital predictor 110 may include an N–M quantity of integrators while the analog approximator 120 may include an k quantity of integrators. The N–M quantity of integrators forming the digital predictor 110 may be configured to accumulate the digital outputs y of the analog approximator 120. Meanwhile, the M quantity of integrators forming the analog approximator 120 may be configured to generate an intermediate output w that may subsequently by quantized the quantizer 140 to generate the digital outputs y.

In the example shown in FIG. 1B, the analog-to-digital converter 100 may be a second order delta sigma modulator including a first integrator 130*a* and a second integrator 130*b*. For example, FIG. 1B shows the digital predictor 110 as including the first integrator 130*a* and the analog approximator 120 as including the second integrator 130*b*. The first integrator 130*a* and the second integrator 130*b* may each include a summation block (e.g., an XOR block) that is coupled in a loop with a comparator block. Nevertheless, it should be appreciated that the analog-to-digital converter 100 may include a different quantity of integrators. Each integrator may serve as a filter (e.g., a low pass filter) capable of removing at least some of the noise in the analog input x and/or the digital output y. Accordingly, increasing the quantity of integrators in the analog-to-digital converter 100 may improve the noise performance (e.g., increased signal to noise ratio (SNR) and/or the like) of the analog-to-digital converter 100.

As noted, the analog approximator 120 may generate, based on the analog input x coupled directly with the analog approximator 120, the digital output y by at least sampling and encoding the input x. Furthermore, the digital predictor 110 may generate, based on the digital output y, the digital prediction p indicative of the expected amplitude of the analog input x. For example, the digital predictor 110 may generate the digital prediction p based on a polarity (e.g., positive or negative) of a succession of the digital outputs y. Because the analog-to-digital converter 100 operate as a delta-sigma modulator, the polarity of each digital output y may indicate whether the amplitude of the analog signal x has increased or decreased since a previous digital output y. A succession of positive or negative digital outputs y may therefore indicate that the amplitude of the analog signal x is increasing or decreasing, for example, past the current dynamic range of the analog approximator 120. By contrast, a succession of digital outputs y having alternating polarities may indicate that the amplitude of the analog signal x is remaining relatively steady.

The digital predictor 110 may generate the digital prediction p to indicate the expected amplitude of the analog input x. For instance, the expected amplitude of the analog input x may exceed the dynamic range of the analog approximator 120 if an a quantity (e.g., 5 or a different quantity) of successive digital outputs y have a same polarity. Alternatively, the expected amplitude of the analog input x may remain within the dynamic range of the analog approximator 120 if a b quantity (e.g., 3 or a different quantity) of successive digital outputs y having alternating polarities.

The dynamic range of the analog approximator 120 may be adjusted based at least on the digital prediction p. The dynamic range of the analog approximator 120 may correspond to the maximum and/or minimum amplitude of the analog input x that may be encoded by the quantizer 140. However, the dynamic range of the analog approximator may depend on the resolution of the quantizer and not the actual magnitude of the analog input x. For instance, the quantizer 140 may encode a large-amplitude analog input x if the quantization step size of the quantizer 140 is sufficiently large. Increasing the quantization step size of the quantizer 140 may increase the size of the interval covered by each value from the finite set of discrete values used to quantize the analog input x. For example, the same quantity of discrete values may be used even when the amplitude of the analog input x increases if the portion of the range of the amplitude covered by each discrete value is increased accordingly.

As such, according to some example embodiments, the quantizer 140 may be an autoranging quantizer whose resolution may be varied by at least changing the quantization step size of the quantizer 140. For instance, the quantizer 140 may respond to prediction p indicating that expected amplitude of the analog input x exceeds the dynamic range of the analog approximator 120 by at least increasing the quantization step size (e.g., by a factor of 2) of the quantizer 140 to expand the dynamic range of the analog approximator 120. Alternatively, the quantizer 140 may respond to the digital prediction p indicating that the expected amplitude of the analog input x is settling within the dynamic range of the analog approximator 120 by decreasing the quantization step size (e.g., by a factor of 2) at the quantizer 140 to contract the dynamic range of the analog approximator 120.

As shown in FIG. 1B, an analog input u entering the digital predictor 110 may be zeroed to remove instability in the operation of the analog-to-digital converter 100. Otherwise, the analog-to-digital converter 100 may be prone to saturation when the analog input u does not stay near zero (e.g., u≈0), which is frequently the case when the analog input u is a neural electrophysiological signal contaminated with large-amplitude transients. To prevent saturation of the analog-to-digital converter 100, the analog input u entering the first may be zeroed while the analog input x may be coupled directly with the analog approximator 120. In the example of the analog-to-digital converter 100 shown in FIG. 1B, the zeroed analog input u may be summed (e.g., by an XOR operation) with the digital output y from the quantizer 140 of the analog approximator 120. Alternatively, as FIG. 1C shows, the digital output y from the quantizer 140 of the analog approximator 120 may be coupled directly with the first integrator 130*a* of the digital predictor 110.

Referring now to FIG. 1C, the second integrator 130*b* may continuously integrate the residue between the time-varying input x(t) and the piecewise constant digital prediction p[n] in accordance with Equation (1) below to generate an intermediate output w[n+1] that is then encoded by the quantizer 140 to generate the digital output y.

$$w[n+1] = w[n] + \frac{1}{T} \int_{nT}^{(n+1)T} (x(t) - p[n]) dt \quad (1)$$

As shown in FIG. 1C, the digital prediction p[n] may be generated by summing (e.g., by performing an XOR operation) the current digital output y[n] with the time integral of digital outputs y [n]. The digital prediction p[n] may be determined by the first integrator 130a in accordance with Equation (2) below.

$$p[n] = -v[n] + y[n] = \Sigma_{i=0}^{\infty} y[n-i] + y[n] \quad (2)$$

Meanwhile, the analog input x may be reconstructed based on the digital outputs y[n] in accordance with Equation (3) below.

$$x[n] = \frac{1}{T} \int_{nT}^{(n+1)T} x(t) dt = \sum_{i=0}^{\infty} y[n-i+1] - (e[n+1] - e[n]) \quad (3)$$

wherein e [n] may denote the quantization error present in the digital outputs y [n].

Equation (4) below may express an radix-2 autoranging of the quantizer 140 in which the quantization step size of the quantizer 140 may vary by a factor of 2.

$$y[n] = 2^{E[n]} D[n] \quad (4)$$

wherein $D[n] = \text{sgn}(w \cdot [n])$ may denote the history of the digital outputs y[n] from the quantizer 140. For example, the $D[n] = -D[n-1]$ may indicate a change in polarity between two successive digital outputs y. By contrast, $D[n] = D[n-1]$ may indicate that two successive digital outputs y may be associated with the same polarity.

As noted, the digital predictor 110 may generate the digital prediction p to indicate the expected amplitude of the analog input x. The expected amplitude of the analog input x may exceed the dynamic range of the analog approximator 120 if an a quantity (e.g., 5 or a different quantity) of the previous digital outputs y[n] have a same polarity. Alternatively, the expected amplitude of the analog input x may be settling within the dynamic range of the analog approximator 120 if a b quantity (e.g., 3 or a different quantity) of the previous digital output y have alternating polarities.

The logic implemented by the digital predictor 110 may be expressed by Equation (5) below. The value of E[n] may be incremented or decremented in order to increase or decrease the quantization step size of the quantizer 140 and in turn the dynamic range of the analog approximator 120.

$E[n] \leftarrow E[n-1]+1$, if $D[n] = \ldots = D[n-4]$;

$E[n] \leftarrow E[n-1]-1$, if $D[n] = -D[n-1] = D[n-2]$; and $E[n] \leftarrow E[n-1]$ otherwise $\quad (5)$ In accordance with Equation (5), when five successive digital outputs y have a same polarity (e.g., $D[n] = \ldots = D[n-4]$), the value of E[n] may be incremented to effect a factor of 2 increase in the quantization step size of the quantizer 140. By contrast, when three successive digital outputs y have alternating polarities (e.g., $D[n] = -D[n-1] = D[n-2]$), the value of E[n] may be decremented to effect a factor of 2 decrease in the quantization step size of the quantizer 140. Otherwise, the value of E[n] may remain the same such that the quantization step size of the quantizer 140 also remains the same.

Figure 2A:
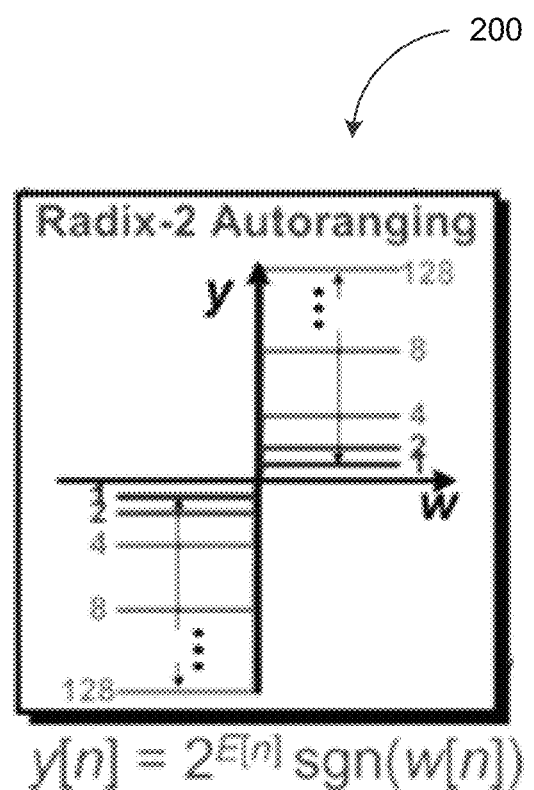
FIG. 2A depicts a graph illustrating quantizer autoranging, in accordance with some example embodiments.
Figure 2B:
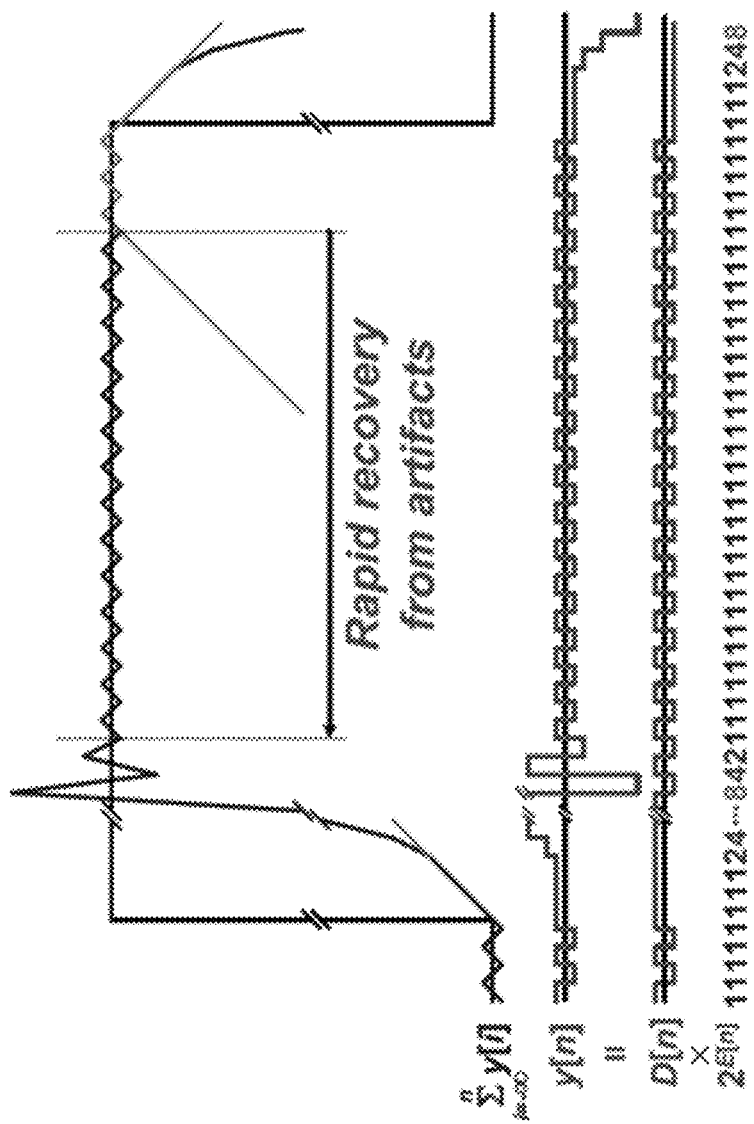
FIG. 2B depicts an effect of digital prediction based autoranging on the output of an analog-to-digital converter, in accordance with some example embodiments.

FIG. 2A depicts a graph 200 illustrating quantizer autoranging, in accordance with some example embodiments. As noted, the history of the previous digital outputs y[n] (e.g., $D[n] = \text{sgn}(w \cdot [n])$) may trigger an expansion or contraction in the dynamic range of the analog approximator 120. For example, FIG. 2A shows that changes in the value of the exponent E[n] (e.g., $E[n] = \{0, 1, \ldots, 7\}$) may cover multiple octaves (e.g., 7 octaves) in digital gain in the digital outputs y [n]. That is, the dynamic range of the analog approximator 120 may expand or contract to accommodate the analog input x even as the amplitude of the analog input x spikes due to the presence of large-amplitude transients.

FIG. 2B depicts an effect of digital prediction based autoranging on the output of the analog-to-digital converter 100, in accordance with some example embodiments. As shown in FIG. 2B, the analog-to-digital converter 100 may be able to respond to a large-amplitude transient contaminating the analog input x, for example, by increasing the quantization step size of the quantizer 140, such that the dynamic range of the analog approximator 120 may increase to accommodate the large-amplitude transient. The presence of the large-amplitude transient may be detected based on an a quantity (e.g., 5 or a different quantity) of successive digital outputs y [n] having a same polarity. By contrast, the quantization step size of the quantizer 140 may subsequently be decreased when the amplitude of the analog input x settles within the dynamic range of the analog approximator 120. Increasing the quantization step size at the quantizer 140 may expedite the recovery of the analog approximator 120 when the analog approximator 120 encounters a large-amplitude transient. Otherwise, if the dynamic range of the analog approximator 120 remains fixed, subjecting the analog approximator 120 to a large-amplitude transient may saturate the analog approximator 120 and cause the output of the analog approximator 120 to remain skewed until it decays back to the dynamic range of the analog approximator 120.

Figure 3A:
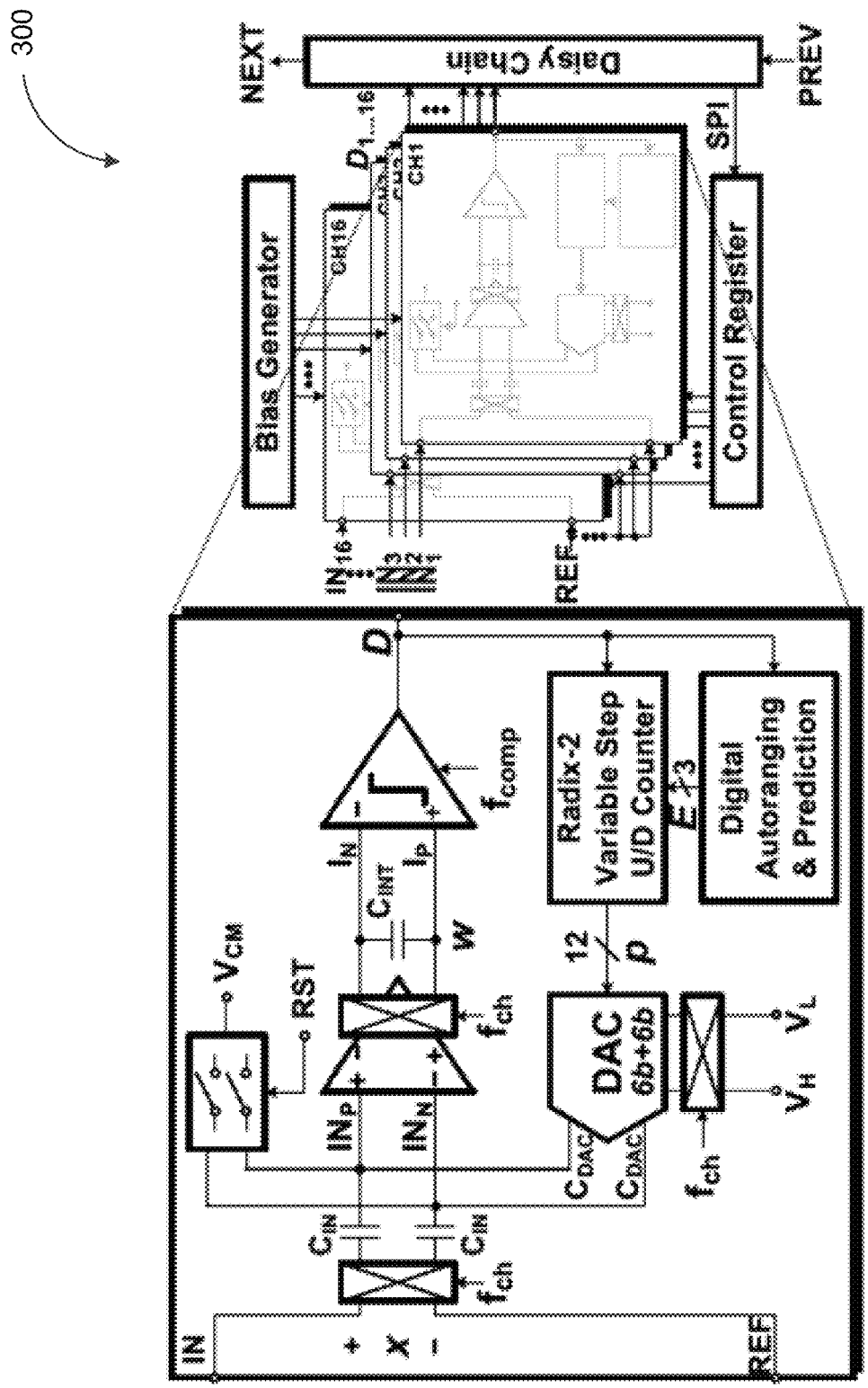
FIG. 3A depicts a schematic diagram illustrating a multi-channel neural-signal-acquisition integrated circuit, in accordance with some example embodiments.
Figure 3B:
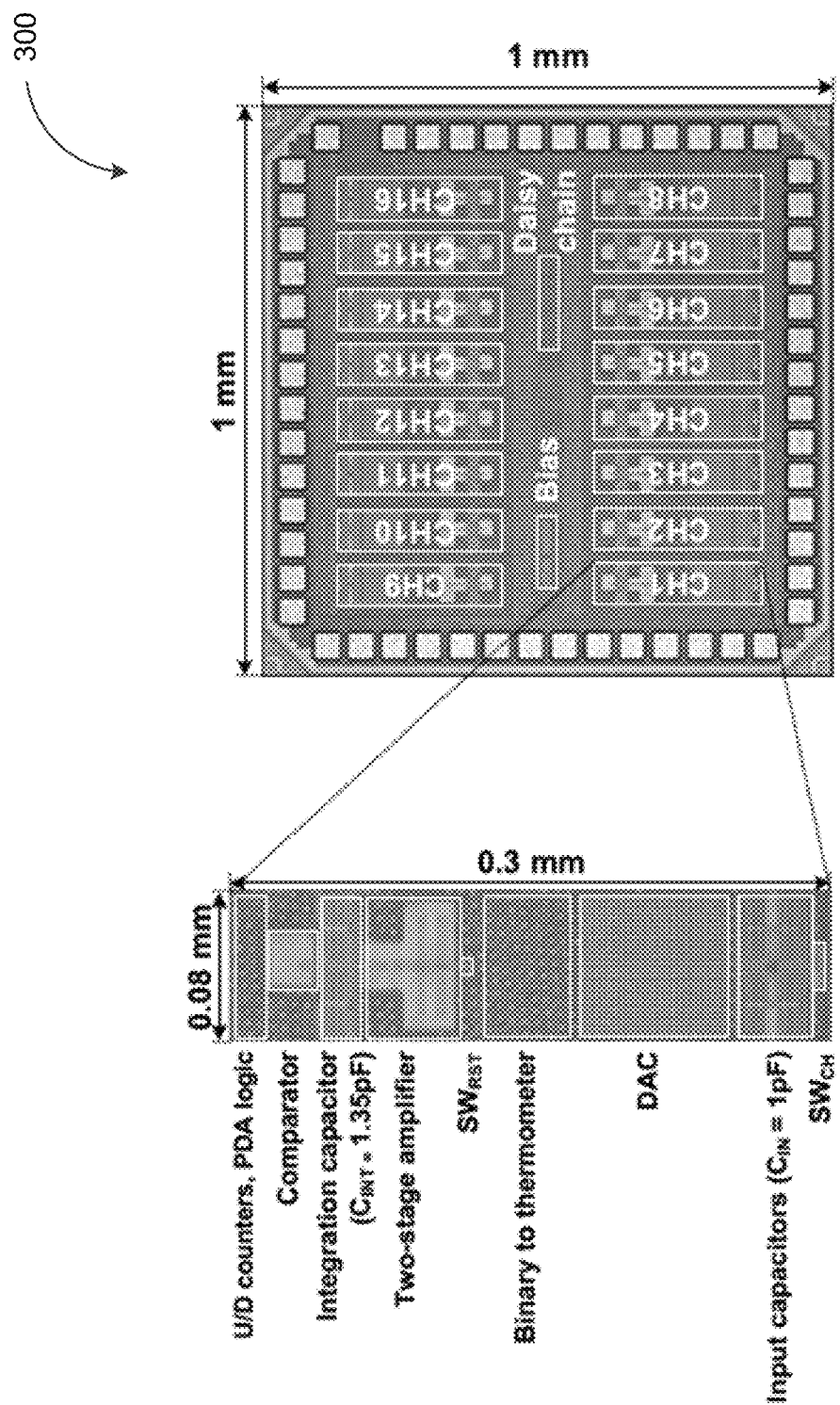
FIG. 3B depicts a micrograph illustrating a multi-channel neural-signal-acquisition integrated circuit, in accordance with some example embodiments.

FIG. 3A depicts a schematic diagram illustrating a multi-channel neural-signal-acquisition integrated circuit 300, in accordance with some example embodiments. Meanwhile, FIG. 3B depicts a micrograph illustrating the multi-channel neural-signal-acquisition integrated circuit 300, in accordance with some example embodiments. In some example embodiments, the multi-channel neural-signal acquisition integrated circuit 300 may include 16 channels, each of which being implemented using the analog-to-digital converter 100 shown in FIGS. 1A-C. For example, the analog-to-digital converter 100 may digitally predict the presence of large-amplitude transients in the analog input x at a 12-bit resolution from a single-bit quantization of the continuously integrated residue between the time-varying analog input x and the piecewise constant digital prediction p[n] at an effective 32 oversampling ratio.

As shown in FIG. 3A, the continuous analog input x(t) may be chopped while its digital prediction p[n] may be reconstituted by a correspondingly reference-chopped digital-to-analog converter (DAC). The analog input x(t) may be further reconstructed by constructing the difference through capacitive coupling to the differential inputs $IN_p$ and $IN_p$ of a transconductance amplifier. For a low-noise implementation, no specific sampling process through switching of capacitors may be utilized and the analog signal x may couple to the amplifier input entirely through charge redistribution in capacitive coupling, thereby avoiding $$\frac{kT}{C}$$
switching noise altogether. The common-mode direct current (DC) bias at the $IN_p$ and $IN_p$ input nodes may be set to $V_{CM}$ by at least activating two switches at power-on reset. Thereafter, the two switches may be deactivated and may remain off throughout the operation analog-to-digital converter 100. Junction diode leakage to bulk connections of these switches towards $V_{CM}$ may maintain the common-mode direct current bias with TΩ-range impedance, with no need for periodic reset.

The resulting residue x(t)−p[n] may be transconductance amplified and unchopped to baseband for continuous-time integration onto $C_{INT}$. A dynamic comparator may generate the binary quantizer output D[n], which through barrel-shifting logic may be combined with autoranging exponent E[n] to produce the digital output y[n] shown in FIGS. 1A-C. The digital prediction p[n] may in turn be obtained as the instantaneous sum of the digital feedback y[n] and its running accumulation as part of one feedback loop in the second order delta sigma modulator forming the analog-to-digital converter 100.

The 15 channels of the multi-channel neural-signal acquisition integrated circuit 300 may share a common reference signal, bias signal, and control signal. Furthermore, FIG. 3A shows their respective outputs $D_1, \ldots, _{16}$ as being daisy-chained at the output to enable higher channel counts through a cascaded multi-chip configuration. The multi-channel neural-signal acquisition integrated circuit 300 may be millimeter in scale. For instance, FIG. 3B shows the multi-channel neural-signal acquisition integrated circuit 300 as measuring 1 mm×1 mm, with each of the 16 channels occupying 0.024 mm², in 65-nanometer low-power bulk complementary metal-oxide-semiconductor (CMOS). The realized capacitance values for $C_{IN}$ and $C_{INT}$ may be 1 picofarad (pF) and 1.35 picofarads, respectively, while the effective capacitance $C_{DAC}$ of the digital-to-analog converter (DAC) may be 128 femtofarad (fF).

Figure 4A:
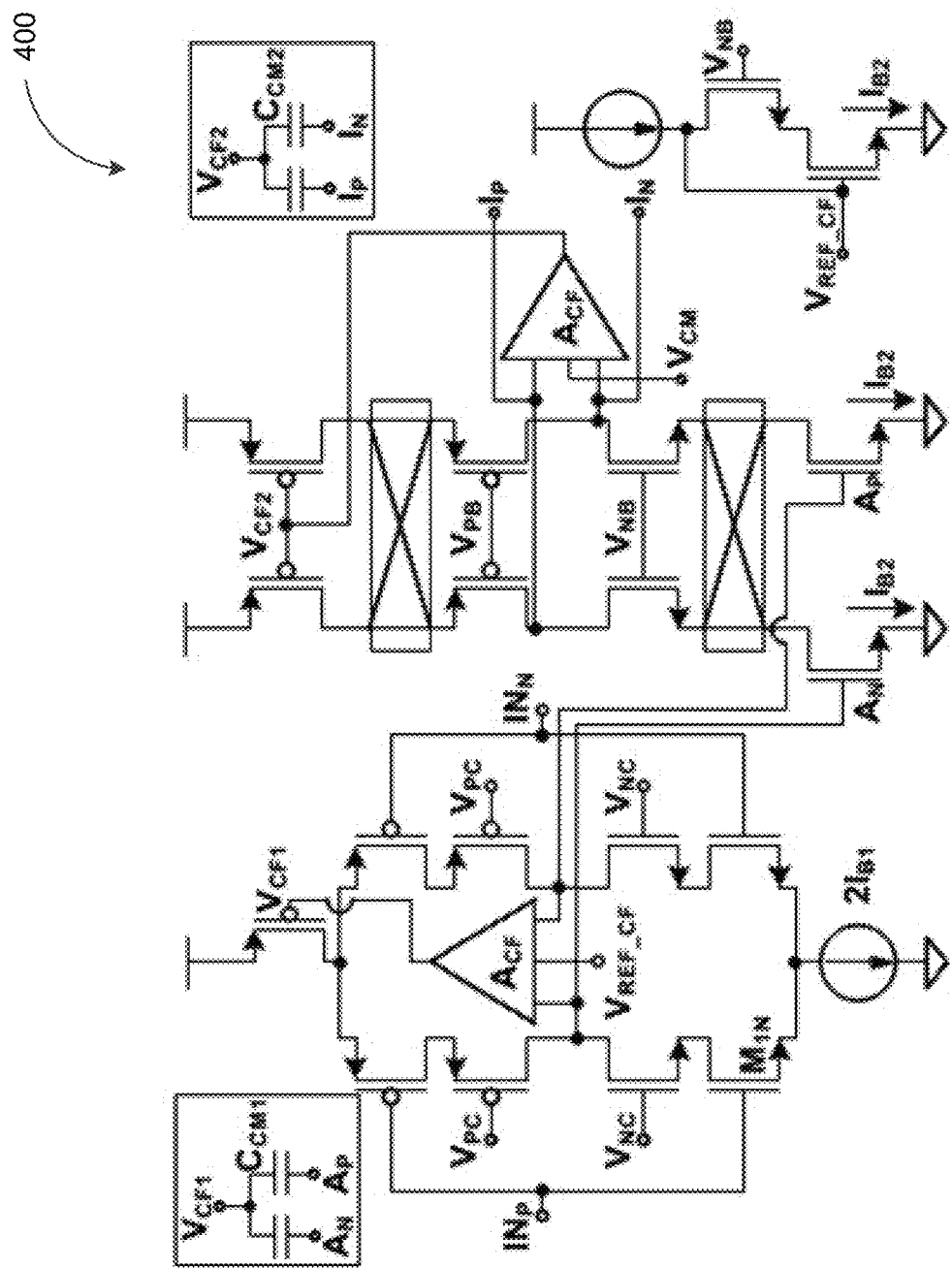
FIG. 4A depicts a schematic diagram illustrating an amplifier, in accordance with some example embodiments.

FIG. 4A depicts a schematic diagram illustrating an amplifier 400, in accordance with some example embodiments. In some example embodiments, the amplifier 400 may be a 2-stage fully differential amplifier with two independent stages of common-mode feedback that feeds into the integration capacitor $C_{INT}$. The amplifier 400 may be configured to activate the digital predictor 110 of the analog-to-digital converter 100. Current biases for $I_{B1}$ and $I_{B2}$ may be set to 375 nanoamperes (nA) and 25 nanoamperes. Current-reusing n-channel metal-oxide-semiconductor field-effect transistor (NMOS) and p-channel metal-oxide-semiconductor field-effect transistor (PMOS) input pairs in the first stage may boost the transfer conductance of the amplifier 400 to 22 microsiemens (μS), thereby improving the noise efficiency factor (NEF) of the amplifier 400. Meanwhile, 600 mV$_{pp}$ output swing at the 0.8-volt supply in the second stage may increase the spurious-free dynamic range of the amplifier 400. The simulated signal gain of the first integrator 130a in the digital predictor 110 may exceed 46 decibels (dB) near the 32 kilohertz (kHz) chopping frequency. Auxiliary amplifiers $A_{CF}$ with conventional n-channel metal-oxide-semiconductor field-effect transistor (NMOS) input differential pairs may implement low-frequency common-mode feedback in each of the two stages of the analog-to-digital converter 100, whereas capacitances $C_{CM1}$=15 femtofarad and $C_{CM2}$=8 femtofarad Miller-boosted for common-mode signals may stabilize common-mode feedback loops.

Figure 4B:
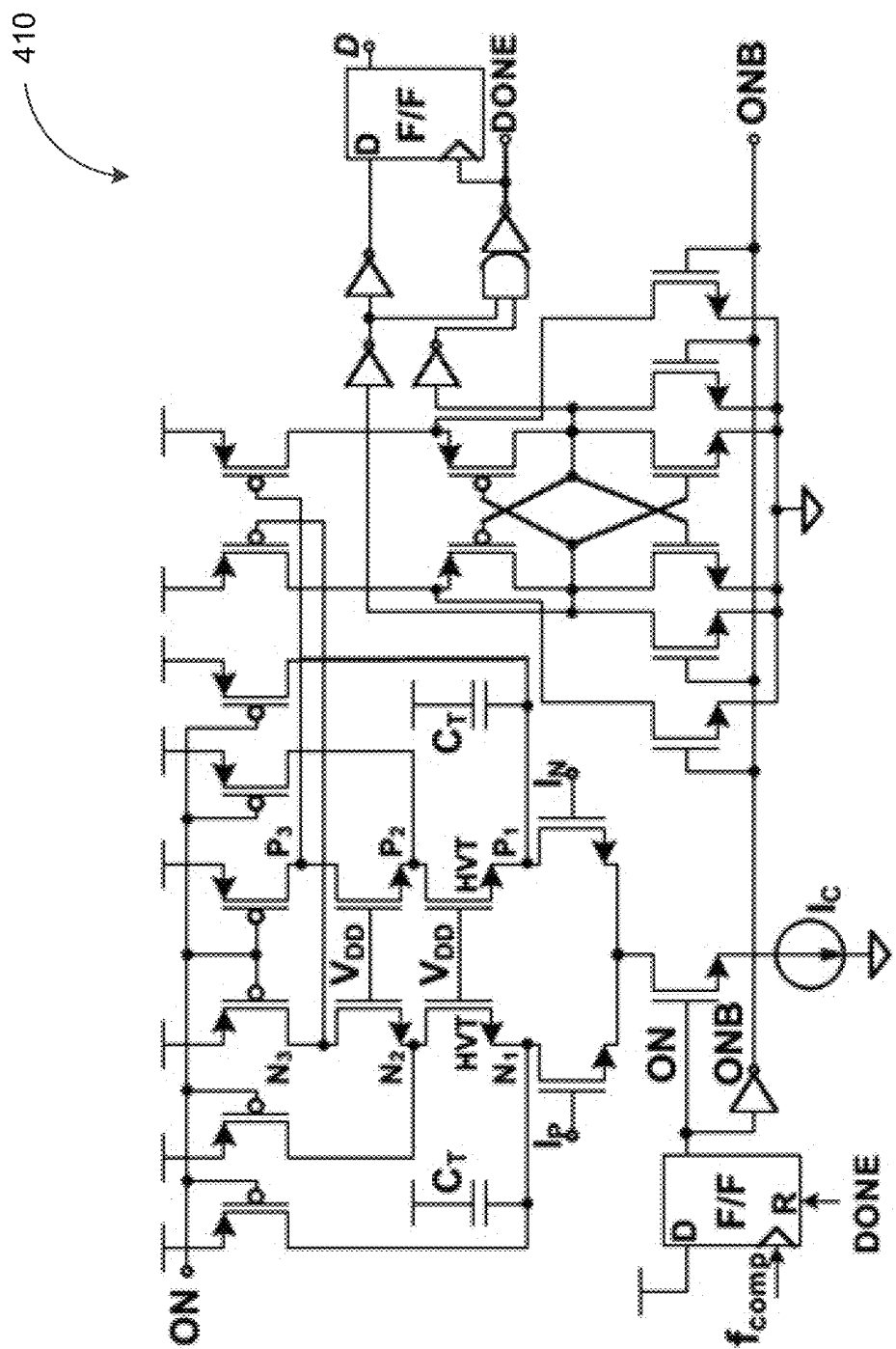
FIG. 4B depicts a schematic diagram illustrating a comparator, in accordance with some example embodiments.

FIG. 4B depicts a schematic diagram illustrating a comparator 410, in accordance with some example embodiments. Referring to FIGS. 1B-C and 4B, the comparator 410 may be a two-stage comparator implementing the quantizer 140. For example, the example of the comparator 410 shown in FIG. 4B may be configured to perform 1-bit quantization that maps the value of a sample of the analog input x to one of two values that may be represented using a single bit. Decision time of the comparator 140 may range from 1.5 microseconds (μs) to 2 microseconds depending on the amplitude of the analog input x, as dominated by the capacitive loading ($C_T$=20 femtofarad) of the first-stage current-starved ($I_C$=20 nanoamperes) pre-amplifier. Owing to the pre-amplification stage, simulated input-referred noise (INR) of the comparator 410 may be less than 80 μV$_{rms}$. At 32 kilohertz operation, the comparator 410 may draw less than 3 nanoamperes of current from a 0.8 volt supply. The ONB clock signal, utilized in subsequent digital logic stages, may be asserted when a decision is made at the comparator 410.

Figure 4C:
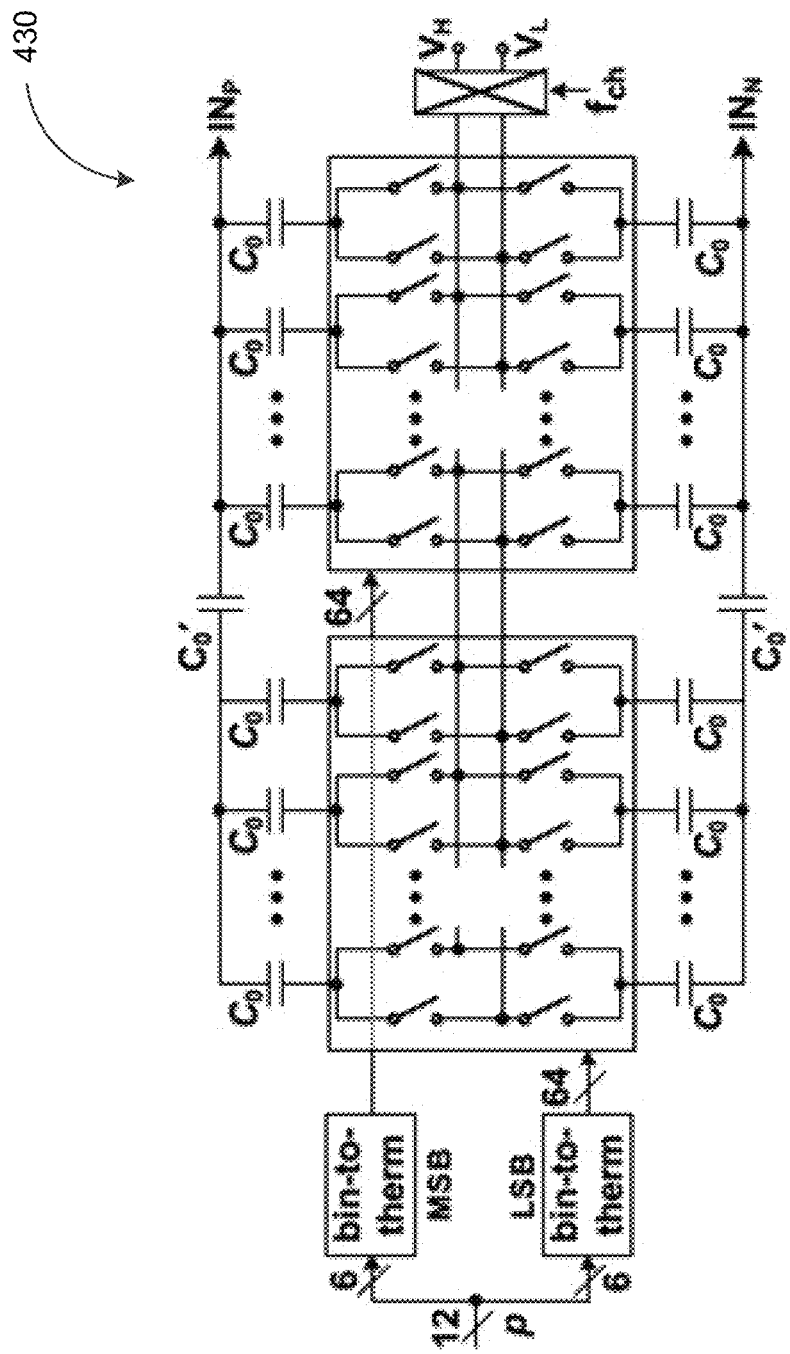
FIG. 4C depicts a schematic diagram illustrating a digital-to-analog converter, in accordance with some example embodiments.

FIG. 4C depicts a schematic diagram illustrating a digital-to-analog converter 420, in accordance with some example embodiments. In some example embodiments, the digital-to-analog converter (DAC) 420 may be implemented with two 64-element custom arrays of 2 femtofarad (fF) unit capacitors $C_0$, each of which being bridged by a 4% larger capacitor $C_0'$. The digital-to-analog converter 420 may be associated with reference levels $V_H$ and $V_L$ tied to the supplies $V_{DD}$=0.8 V and $V_{SS}$=0 V. While current consumption from $V_H$ may be 50 nanoamperes, digital logic within the digital-to-analog converter may consume 10 nanoamperes from the 0.8 V supply at 32 kilohertz.

Figure 5A:
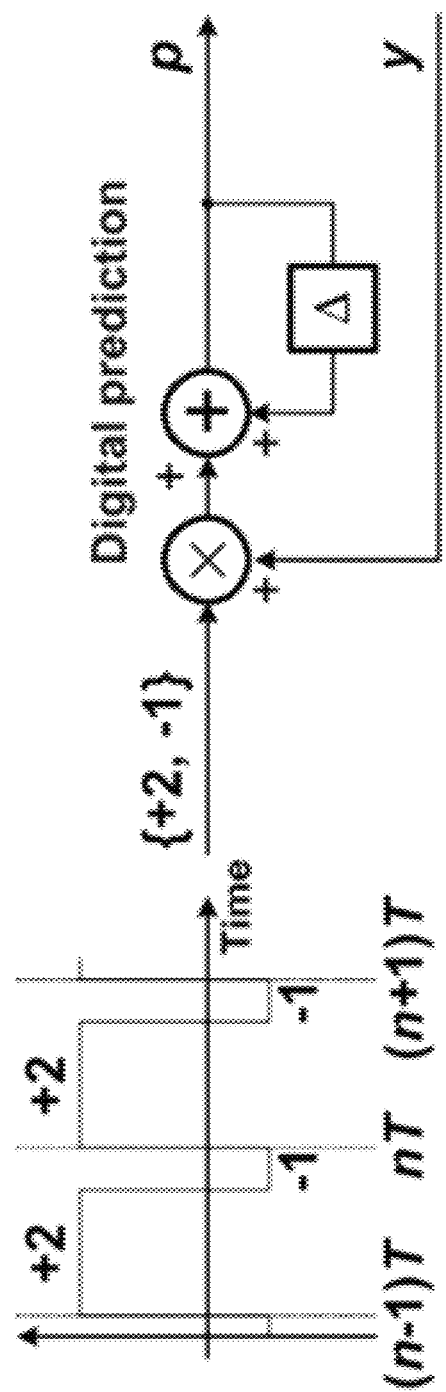
FIG. 5A illustrates the activation of a digital predictor of an analog-to-digital converter, in accordance with some example embodiments.
Figure 5B:
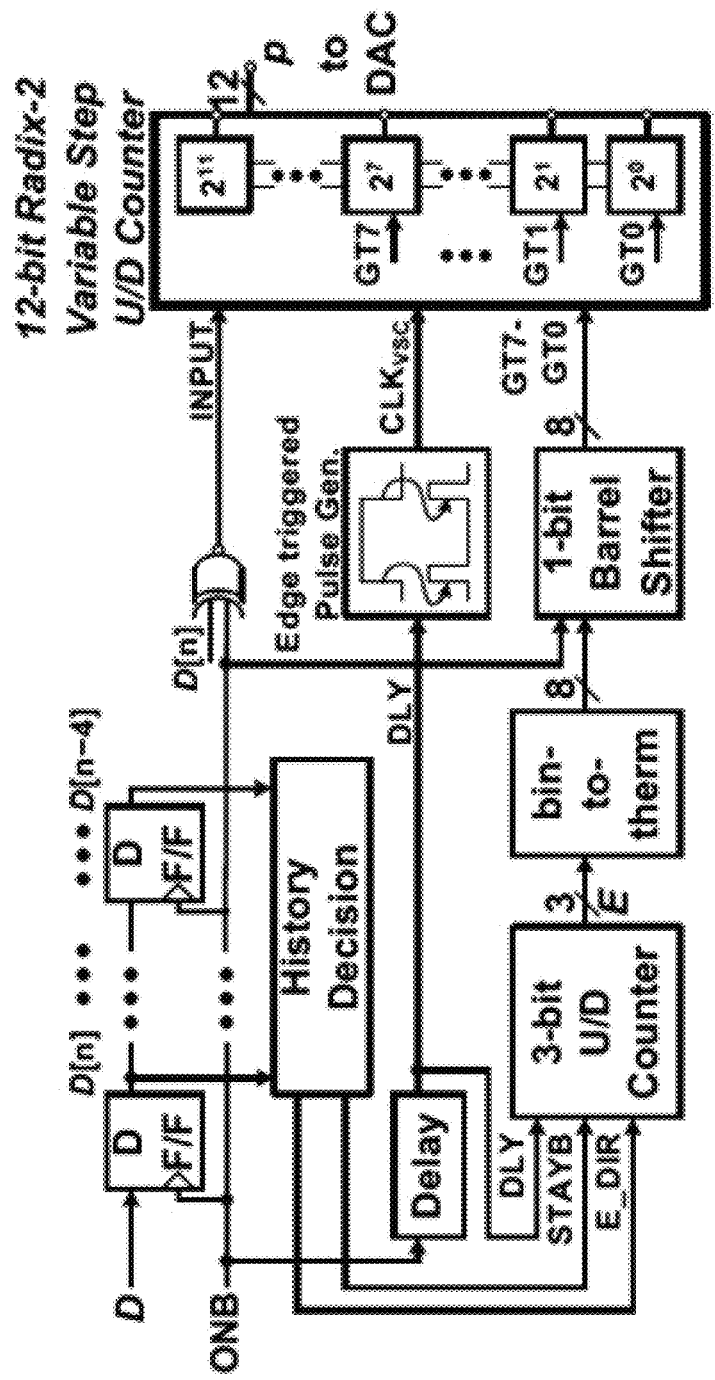
FIG. 5B illustrates the logic of an analog-to-digital converter, in accordance with some example embodiments.
Figure 5C:
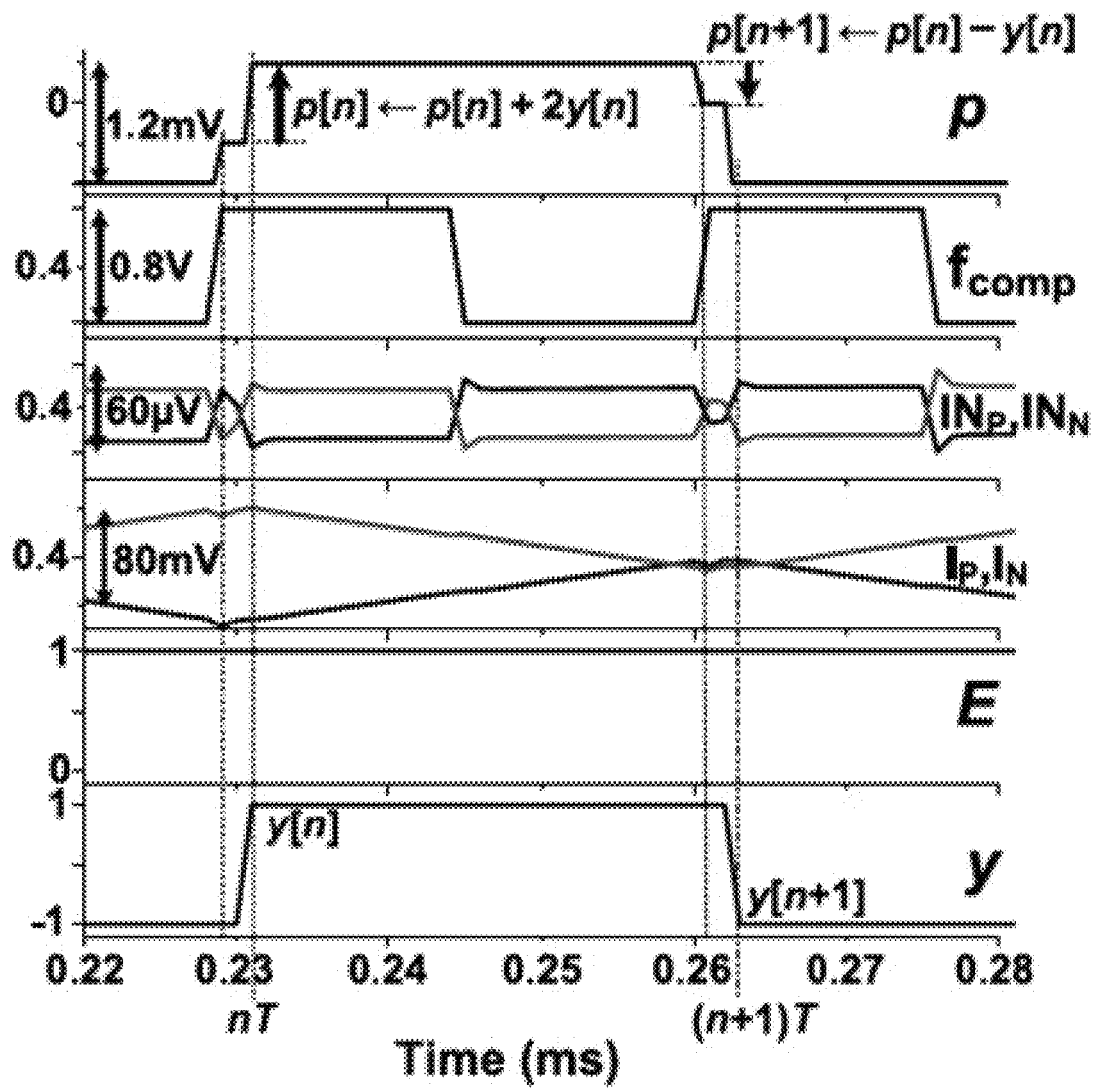
FIG. 5C depicts time-domain waveforms illustrating the internal operations of an analog-to-digital converter, in accordance with some example embodiments.

FIGS. 5A-C illustrates the implementation and timing control of the analog-to-digital converter 100 including the digital predictor 110 and the analog approximator 120. In some example embodiments, a 12-bit radix-2 variable-step up/down counter may update the digital prediction p[n] from the digital predictor 110 in two phases. First, a double increment/decrement operation p[n]←p[n]+2y[n] may activate the counter at the binary input position E[n]+1 while a subsequent retracting operation with opposite polarity p[n]←p[n]−y[n] may activate the counter at the binary input position E[n] just prior to the next cycle. Timing of the two-phase updates of the digital prediction state variable p[n] may be triggered by the initiation and settling of the comparator output through the ONB signal as shown in FIG. 5B. The thermometer-coded (GT0, . . . GT7) binary input position E[n] of the radix-2 variable-step up/down counter may be dynamically incremented or decremented by one point, or may stay put, depending on the stored history in the quantization bits D[n], . . . , D[n−4]. It should be appreciated that the operations of the analog-to-digital converter 100 implementing this logic may consume less than 12 nanowatts (nW) of power at 32 kilohertz.

Figure 6A:
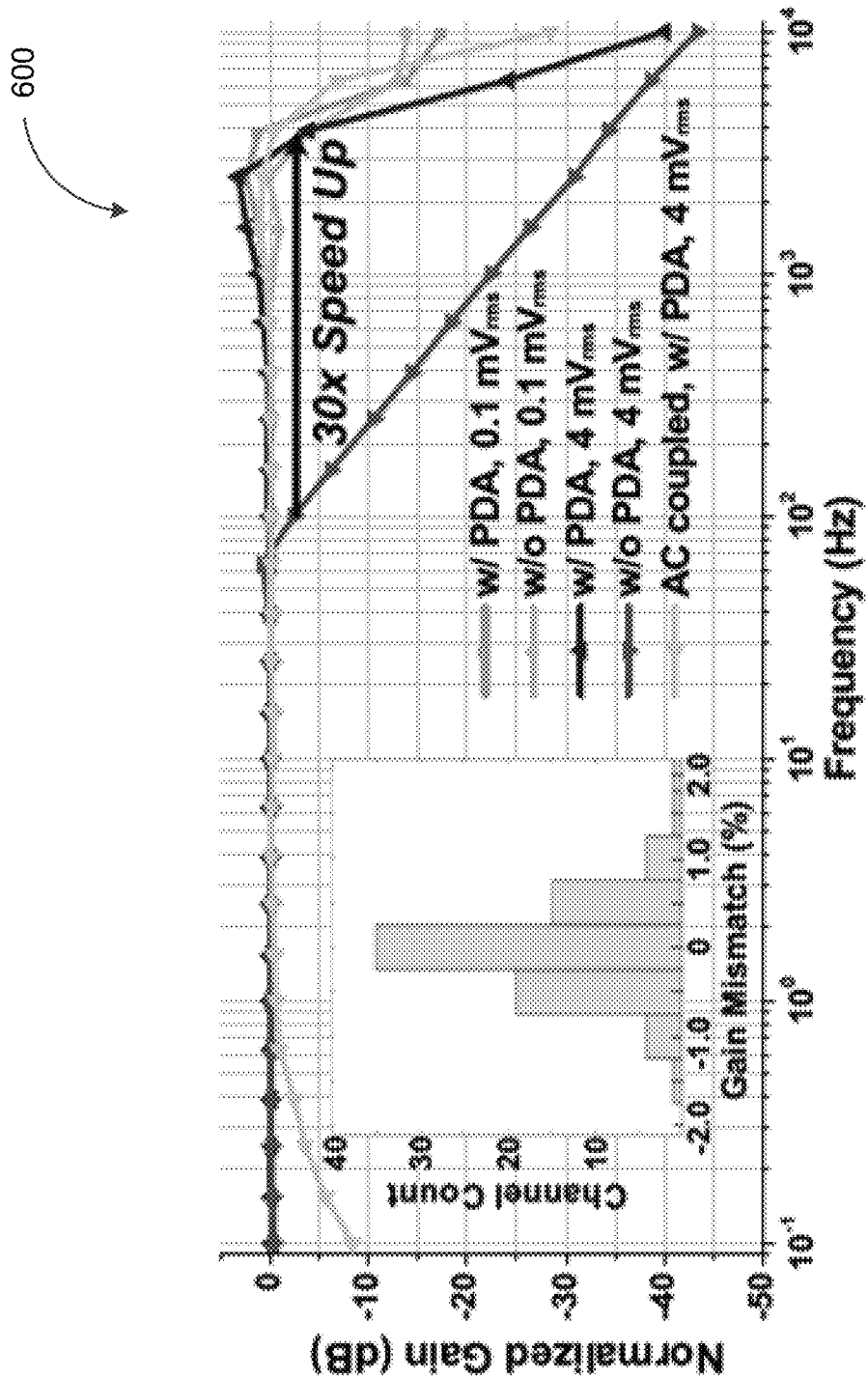
FIG. 6A illustrates the effects of predictive digital autoranging on signal-dependent gain, in accordance with some example embodiments.

FIG. 6A illustrates the effects of predictive digital autoranging on signal-dependent gain, in accordance with some example embodiments. In the absence of predictive digital autoranging, the response to a large-amplitude transient may be slew-rate-limited due to unity increments/decrements in the digital feedback. By contrast, with predictive digital autoranging, the response to large amplitude transients (e.g., 4 amplitude signals) demonstrate a 30× improvement in speed. For instance, in the absence of predictive digital autoranging, a large-amplitude transient may start to cutting off at frequencies above 57 hertz at a 32 kilohertz sampling rate, with proportionally higher cut off frequencies at lower signal amplitudes (e.g., 2.3 kilohertz at 100. The use of predictive digital autoranging may enable the achievement of full bandwidth limited response independent of signal amplitude (e.g., through adjusting the value of the exponent E[n]. The measured 5.95 V/V gain may be flat at low frequencies down to direct current (DC). Measured relative mismatch (e.g., standard deviation over mean) in midband voltage gain may be 4.5% across chips (inter-chip) and 0.7% across channels within the same chip (intra-chip).

Figure 6B:
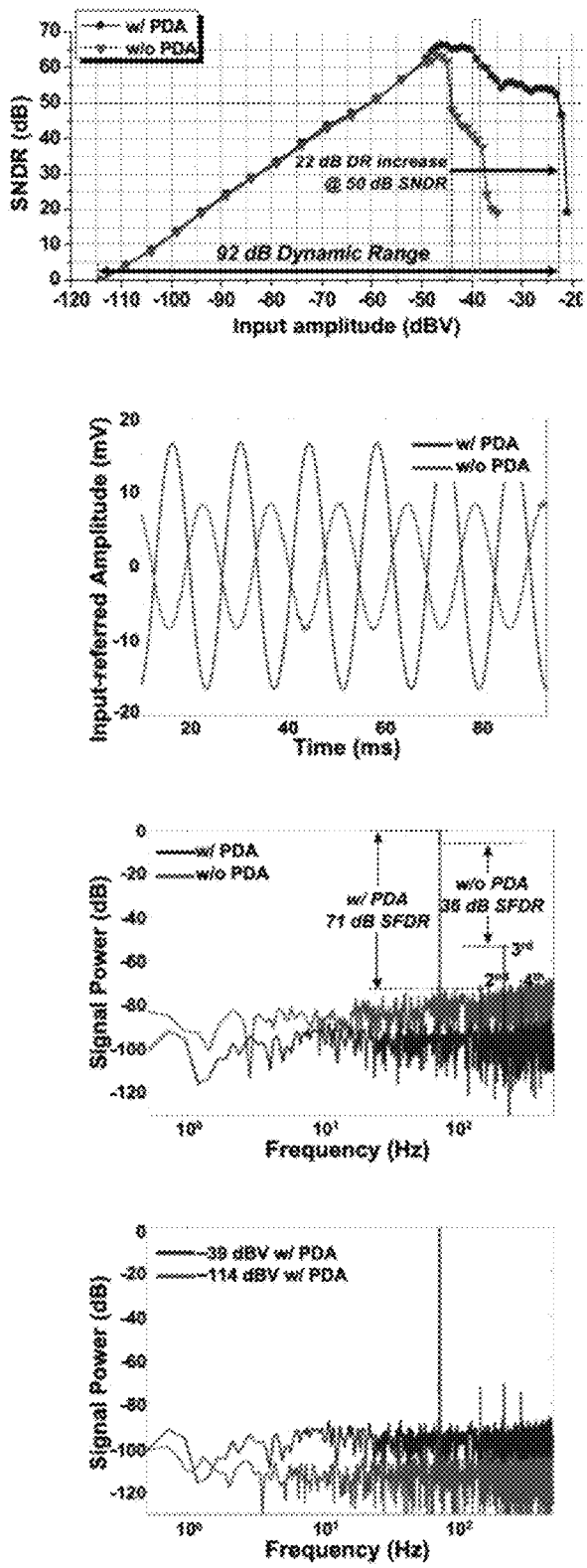
FIG. 6B illustrates the effects of predictive digital autoranging on dynamic range, in accordance with some example embodiments.

The effects of predictive digital autoranging may further include an increase in the dynamic range of the analog-to-digital converter 100. FIG. 6B illustrates the effects of predictive digital autoranging on dynamic range, in accordance with some example embodiments. As shown in FIG. 6B, predictive digital autoranging may extend the dynamic range of the analog-to-digital converter 100 by 22 decibels (dBs) at greater than 50 decibel signal to noise and distortion ratio (SNDR), which approaches the full-scale 92-decibel dynamic range of the digital-to-analog converter. The observed improvements to signal to noise and distortion ration may be attributed to reduced spurs as well as reduced noise floor, reaching 66 decibel at −39 dB($V_{rms}$) as shown in FIG. 10.

Figure 6C:
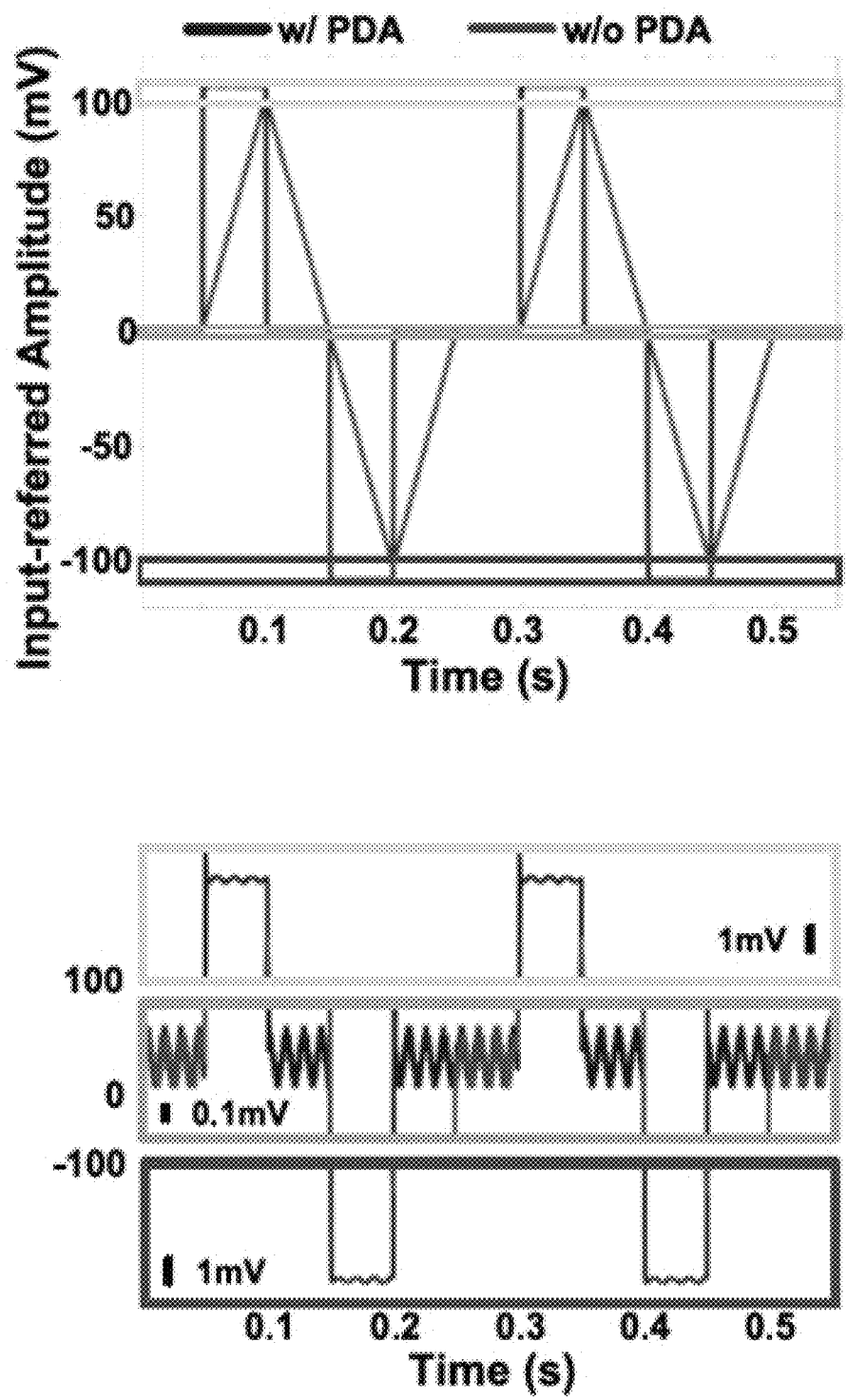
FIG. 6C illustrates the effects of predictive digital autoranging on transient response to large-amplitude artifacts, in accordance with some example embodiments.

As noted, predictive digital autoranging may significantly decrease recovery time for large-amplitude transients. FIG. 6C illustrates the effects of predictive digital autoranging on transient response to large-amplitude artifacts, in accordance with some example embodiments. Recovery time for the analog-to-digital converter 100 implementing predictive digital autoranging may be evaluated using a synthesized waveform from a combination of two signal sources including a 100 $\mu V_{rms}$ sinusoidal signal and a 200 $mV_{PP}$ pulsed artifact transient as shown in FIG. 6C. Predictive digital autoranging may fast tracking of the analog input x such that the analog-to-digital converter implementing predictive digital autoranging may recover from the 200 $mV_{PP}$ transients in less than 1 millisecond. Contrastingly, without predictive digital autoranging, the digital output y may be markedly slew-limited.

Figure 7:
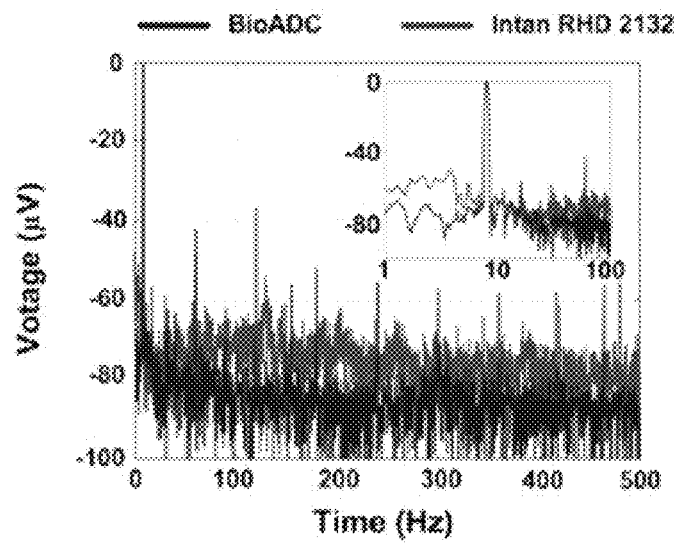
FIG. 7 illustrates the performance of a neural data acquisition system implemented using predictive digital autoranging analog-to-digital converters relative to the performance of a conventional neural data acquisition system implemented without predictive digital autoranging analog-to-digital converters, in accordance with some example embodiments.
Figure 7:
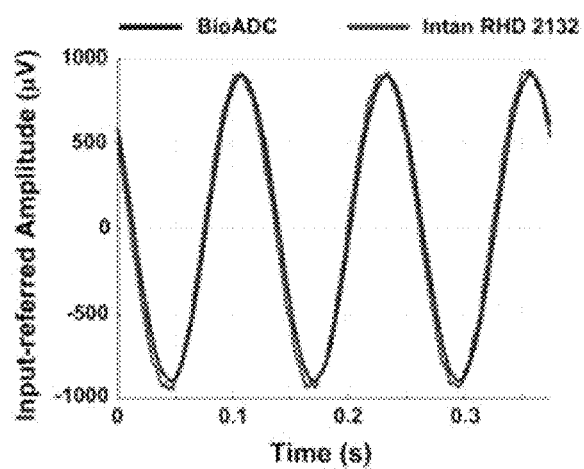
Figure 7:
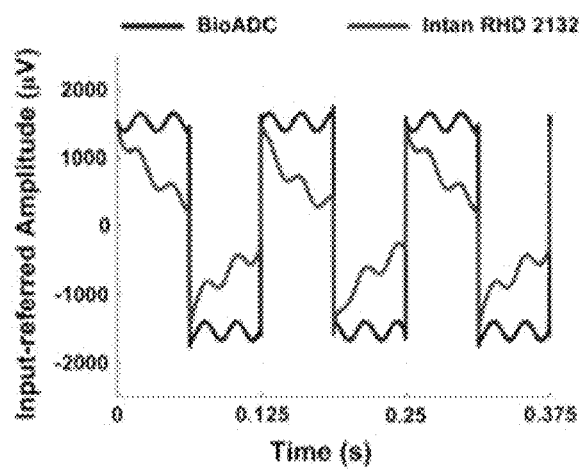

FIG. 7 illustrates the performance of a neural data acquisition system implemented using predictive digital autoranging analog-to-digital converters relative to the performance of a conventional neural data acquisition system implemented without predictive digital autoranging analog-to-digital converters, in accordance with some example embodiments. As FIG. 7 shows, the neural data acquisition system implemented using predictive digital autoranging analog-to-digital converters (e.g., BioADC) consistently demonstrated superior performance in input-referred noise, input dynamic range, and transient response relative to a conventional neural data acquisition system implemented without predictive digital autoranging analog-to-digital converters (e.g., Intan RHD 2132).

Figure 8:
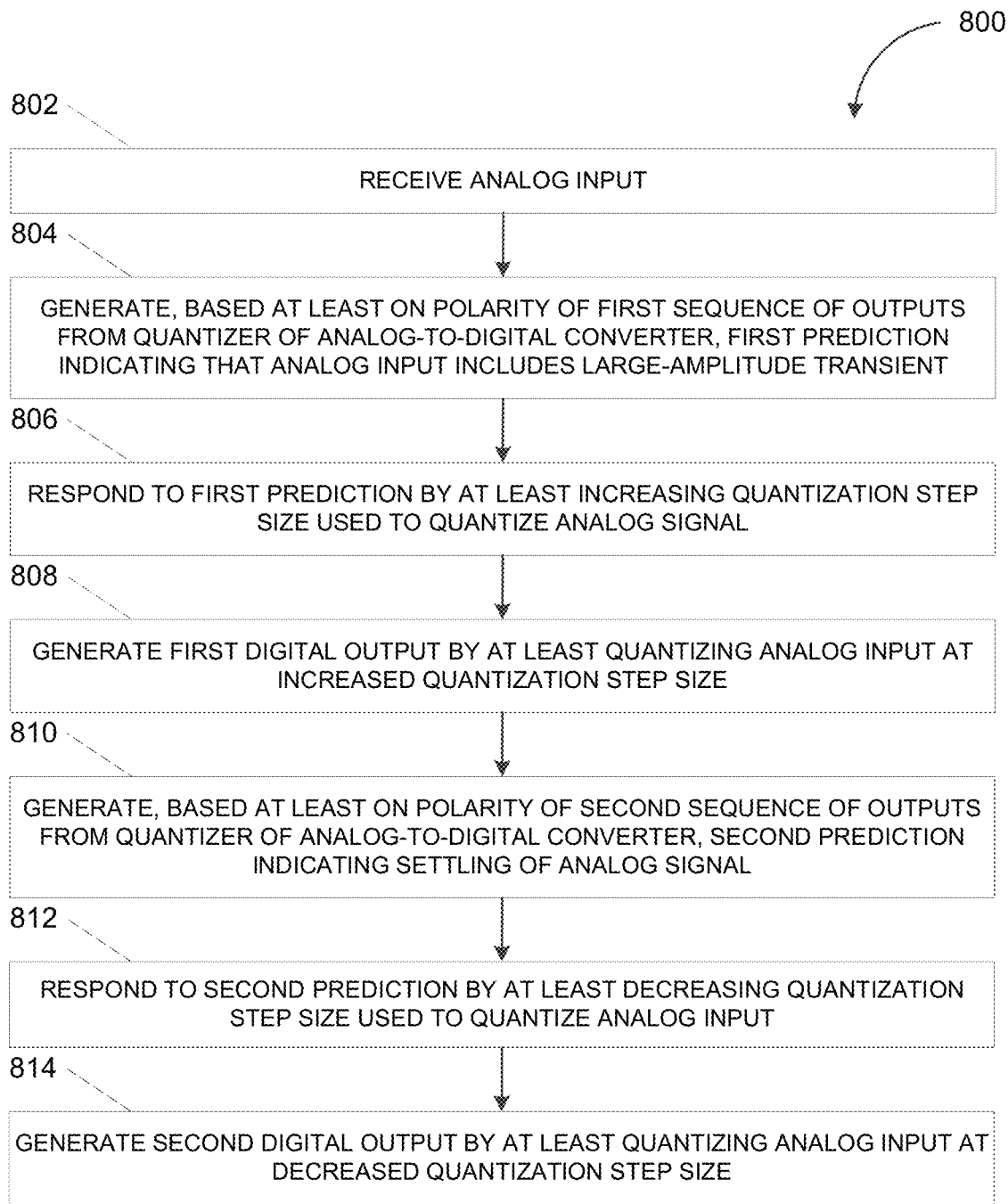
FIG. 8 depicts a flowchart illustrating a process for analog-to-digital conversion, in accordance with some example embodiments.

FIG. 8 depicts a flowchart illustrating a process 800 for analog-to-digital conversion, in accordance with some example embodiments. Referring to FIGS. 1A-C and 8, the process 800 may be performed by the analog-to-digital converter 100.

At 802, the analog-to-digital converter 100 may receive an analog input. In some example embodiments, the analog-to-digital converter 100 may include the digitizing loop 150 formed from the digital predictor 110, the analog approximator 120, and the quantizer 140. The analog-to-digital converter 100 may be an N-th order delta sigma modulator having a net N quantity of integrators in the feedback loop. An N−M quantity of digital integrators (e.g., accumulators) may form the predictor 110 while an M quantity of analog integrators may form the analog approximator 120, whose output is fed into the quantizer 140. As shown in FIGS. 1A-C, the analog input x may be coupled directly with the analog approximator 120 instead of the digital predictor 110 to increase the stability of the N-th order delta sigma modulator forming the analog-to-digital converter 100. In some example embodiments, the analog input x may a neural electrophysiological signal including, for example, local field potential (LFP) signals, electrocorticogram (ECoG) signals, and/or the like.

At 804, the analog-to-digital converter 100 may generate, based at least on a polarity of a first sequence of outputs from the quantizer 140 of the analog-to-digital converter 100, a first prediction indicating that the analog input includes a large-amplitude transient. For example, the digital predictor 110 of the analog-to-digital converter 100 may generate the digital prediction p to indicate the expected amplitude of the analog signal x. A large-amplitude transient may be expected to be present in the analog input x if an a quantity (e.g., 5 or a different quantity) of successive digital outputs y from the analog-to-digital converter 100 have a same polarity. As noted, because the analog-to-digital converter 100 operate as a delta-sigma modulator, a succession of positive or negative digital outputs y may indicate that the amplitude of the analog signal x is increasing or decreasing, for example, past the current dynamic range of the analog approximator 120.

At 806, the analog-to-digital converter 100 may respond to the first prediction by at least increasing a quantization step size used to quantize the analog input. The dynamic range of the analog approximator 120 may correspond to the maximum and/or minimum amplitude of the analog input x that may be encoded by the quantizer 140. However, the dynamic range of the analog approximator may depend on the resolution of the quantizer and not the actual magnitude of the analog input x. For instance, the quantizer 140 may be capable of encoding a large-amplitude analog input x if the quantization step size of the quantizer 140 is sufficiently large. Accordingly, in some example embodiments, the analog-to-digital converter 100 may increase the quantization step size of the quantizer 140 when the digital prediction p indicates that a large-amplitude transient is expected to be present in the analog input x. Increasing the quantization step size (e.g., by a factor of 2) of the quantizer 140 may expand the dynamic range of the analog approximator 120 to accommodate the large-amplitude transient.

At 808, the analog-to-digital converter 100 may generate a first digital output by at least quantizing the analog input at the increased quantization step size. In some example embodiments, the digital output y of the analog-to-digital converter 100 may be generated by the quantizer 140 assigning, to one or more samples of the analog signal x, a value from a finite set of discrete values. When the quantization step size of the quantizer 140 is increased, the quantizer 140 may decrease the resolution at which the analog signal x is being quantized. That is, the same finite set of discrete values may be used to represent a larger range of amplitude at a lower resolution.

At 810, the analog-to-digital converter 100 may generate, based at least on a polarity of a second sequence of outputs from the quantizer 140 of the analog-to-digital converter 100, a second prediction indicating that a settling of the analog input. In some example embodiments, the digital predictor 110 may generate the digital prediction p to indicate that the expected amplitude of the analog input x is settling if a b quantity (e.g., 3 or a different quantity) of successive digital outputs y having alternating polarities. As noted, because the analog-to-digital converter 100 operate as a delta-sigma modulator, a succession of digital outputs y having alternating polarities may indicate that the amplitude of the analog signal x is settling instead of increasing or decreasing.

At 812, the analog-to-digital converter 100 may respond to the second predicting by at least decreasing the quantization step size used to quantize the analog input. For example, when the analog-to-digital converter 100 determines that the amplitude of the analog signal x is settling, which may occur in the absence of large-amplitude transients, the analog-to-digital converter 100 may decrease the quantization step size at the quantizer 140, thereby increasing the resolution at which the analog input x is being quantized by the quantizer 140.

At 814, the analog-to-digital converter 100 may generate a second digital output by at least quantizing the analog input at the decreased quantization step size. As noted, the digital output y of the analog-to-digital converter 100 may be generated by the quantizer 140 assigning, to one or more samples of the analog signal x, a value from a finite set of discrete values. When the quantization step size of the quantizer 140 is decreased, the quantizer 140 may increase the resolution at which the analog signal x is being quantized.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus, comprising:
a first delta sigma modulator, a first portion of the first delta sigma modulator forming a digital predictor, a second portion of the first delta sigma modulator forming an analog approximator, an analog approximation output by the analog approximator being coupled with a quantizer, the digital predictor, the analog approximator, and the quantizer forming a digitizing loop configured to convert an analog input into a digital output, the digital predictor being configured to generate, based at least on a polarity of one or more digital outputs from the quantizer, a digital prediction of an expected amplitude of the analog input, the quantizer being configured to respond to the digital prediction by at least adjusting a dynamic range of the digitizing loop, and the dynamic range of the digitizing loop being adjusted by at least changing a quantization step size used by the quantizer to quantize the analog input.

2. The apparatus of claim 1, wherein the quantizer is configured to quantize the analog approximation by at least outputting, for each sample of the analog approximation, a discrete value from a finite set of discrete values corresponding to an amplitude of each sample of analog approximation.

3. The apparatus of claim 2, wherein the changing of the quantization step size modifies a range of differences between each discrete value in the finite set of discrete values.

4. The apparatus of claim 1, wherein the analog input is oversampled at a frequency above a Nyquist rate.

5. The apparatus of claim 1, wherein the first delta sigma modulator includes an N quantity of integrators chained to form an N quantity of feedback loops, wherein the digital predictor includes an N–M quantity of integrators, and wherein the analog approximator includes a M quantity of integrators.

6. The apparatus of claim 5, wherein the N–M quantity of integrators are configured to accumulate the one or more digital outputs from the quantizer, and wherein the digital predictor generates the digital prediction by at least summing a current digital output from the quantizer with an accumulation of one or more previous digital outputs from the quantizer.

7. The apparatus of claim 1, wherein a digital-to-analog converter is configured to convert the digital prediction into a corresponding analog signal, and wherein a difference between the analog input and the analog signal is coupled with the analog approximator, and wherein the one or more digital outputs from the quantizer are coupled with the digital predictor in a feedback loop.

8. The apparatus of claim 1, wherein an amplitude of the analog input is expected to exceed the dynamic range of the digitizing loop based at least on a threshold quantity of successive digital outputs from the quantizer having a same polarity.

9. The apparatus of claim 8, wherein the quantizer responds to the digital prediction by at least increasing the quantization step size to increase the dynamic range of the digitizing loop.

10. The apparatus of claim 1, wherein an amplitude of the analog input is expected to settle within the dynamic range of the digitizing loop based at least on a threshold quantity of successive digital outputs from the quantizer having alternating polarities.

11. The apparatus of claim 10, wherein the quantizer responds to the digital prediction by at least decreasing the quantization step size to decrease the dynamic range of the digitizing loop.

12. The apparatus of claim 1, wherein changing a quantization step size used to quantize the analog input further changes a resolution of the quantizer.

13. The apparatus of claim 1, wherein the dynamic range of the digitizing loop corresponds to a maximum amplitude and/or a minimum amplitude of the analog input the digitizing loop is able to convert.

14. The apparatus of claim 1, wherein the dynamic range of the digitizing loop is adjusted by a factor of 2.

15. The apparatus of claim 1, wherein the apparatus comprises a multi-channel neural-signal-acquisition system, wherein the apparatus further comprises a second delta sigma modulator, and wherein each of the first delta sigma modulator and the second delta sigma modulator form one of a plurality of recording channels comprising the multi-channel neural-signal-acquisition system.

16. The apparatus of claim 1, wherein the analog input comprises a neural electrophysiological signal.

17. A method, comprising:
receiving, at a delta sigma modulator, an analog input, a first portion of the delta sigma modulator forming a digital predictor, a second portion of the delta sigma modulator forming an analog approximator, an analog approximation output by the analog approximator being coupled with a quantizer, the digital predictor, the analog approximator, and the quantizer forming a digitizing loop configured to convert the analog input into a digital output;
generating, by the digital predictor, a digital prediction of an expected amplitude of the analog input, the digital prediction being generated based at least on one or more digital outputs from the quantizer; and
in response to the digital prediction, adjusting, by the quantizer, a dynamic range of the digitizing loop, the dynamic range of the digitizing loop being adjusted by at least changing a quantization step size used by the quantizer to quantize the analog input.

18. The method of claim 17, wherein an amplitude of the analog input is expected to exceed the dynamic range of the digitizing loop based at least on a threshold quantity of successive digital outputs from the quantizer having a same polarity, and wherein the quantizer responds to the digital prediction by at least increasing the quantization step size to increase the dynamic range of the digitizing loop.

19. The method of claim 17, wherein an amplitude of the analog input is expected to settle within the dynamic range of the digitizing loop based at least on a threshold quantity of successive digital outputs from the quantizer having alternating polarities, and wherein the quantizer responds to the digital prediction by at least decreasing the quantization step size to decrease the dynamic range of the digitizing loop.

20. The method of claim 17, wherein the analog input is converted to the digital output at least by the quantizer quantizing the analog approximation, wherein the analog approximation is quantized by at least assigning, to each sample of the analog approximation, a discrete value from a finite set of discrete values corresponding to an amplitude of the analog approximation.

* * * * *